(12) United States Patent
Hirashima et al.

(10) Patent No.: US 7,598,349 B2
(45) Date of Patent: Oct. 6, 2009

(54) ANTIBODIES TO PEPTIDE FRAGMENTS HAVING CELL DEATH-INHIBITORY ACTIVITY

(75) Inventors: Masaki Hirashima, Kikuchi-gun (JP); Hiroaki Maeda, Kumamoto (JP); Chikateru Nozaki, Kumamoto (JP)

(73) Assignee: Juridical Foundation The Chemo-Sero-Therapeutic Research Institute, Kumamoto-Shi (JP)

( * ) Notice: Subject to any disclaimer, the term of this patent is extended or adjusted under 35 U.S.C. 154(b) by 294 days.

(21) Appl. No.: 11/185,859

(22) Filed: Jul. 21, 2005

(65) Prior Publication Data

US 2005/0281808 A1    Dec. 22, 2005

Related U.S. Application Data

(62) Division of application No. 09/856,199, filed as application No. PCT/JP99/06322 on Nov. 12, 1999, now Pat. No. 7,199,097.

(30) Foreign Application Priority Data

Nov. 19, 1998  (JP) ................................. 10/347863

(51) Int. Cl.
    C07K 16/00     (2006.01)
(52) U.S. Cl. .................................. 530/387.1
(58) Field of Classification Search ...................... None
    See application file for complete search history.

(56) References Cited

OTHER PUBLICATIONS

Himeno et al (J. Biol. Chem. 1996; 271(26):15769-15775).*
Campbell, A (Monoclonal Antibody Technology; 1984; Elsevier Science Publishing Company: pp. 1-33).*
Greenberg S. M., et al., "Characterization of a New Megakaryocytic Cell Line: The Dami Cell", Blood, vol. 72, No. 6, 1988, pp. 1968-1977.
"Catalog No. 1011391: Nutridoma-HU", Roche Molecular Biochemicals Catalogue, Online, Oct. 1999.
MacLeod, R.A.F., et al., "Identity of Original and Late Passage Dami Megakaryocytes with HEL Erythroleukemia Cells Shown by Combined Cytogenetics and DNA fingerprinting", Leukemia, vol. 11, No. 12, Dec. 1997, pp. 2032-2038.
"Using Apoptosis to Screen for Tumour Promoters", Research Disclosure, Kenneth Mason Publications, vol. 427, No. 57, Nov. 1999.
Masaki Hirashima et al.; Biol. Pharm. Bull., vol. 26, No. 6, pp. 794-798 (2003).
Hill et al., Proc. Natl. Acad. Sci, vol. 90, No. 2, pp. 537-541 (1993).
Akesson et al., Biochim. Biophys. Acta, vol. 1204, No. 2, pp. 243-249 (1994).
Hill et al., J. Nutr. vol. 126, No. 1, pp. 138-145 (1996).
Persson-Moschos et al., Analyst, vol. 120, No. 3, pp. 833-836 (1995).
Arteel et al., Biol. Chem. vol. 379, Nos. 8-9 (Aug.-Sep. 1998).
Craig B. Thompson, Science, vol. 267, Mar. 10, 1995, pp. 1456-1462.
Lixin Zheng et al., Nature, vol. 377, Sep. 28, 1995, pp. 348-351.
Takashi Suda et al., Cell, vol. 75, Dec. 17, 1993, pp. 1169-1178.
A. H. Wyllie, Nature, vol. 284, Apr. 10, 1980, pp. 555-556.
Lawrence H. Boise et al., Cell, vol. 74, Aug. 27, 1993, pp. 597-608.
Laura J. S. Greenlund et al., Neuron, vol. 14, Feb. 1995, pp. 303-315.
Paul A. Sandstrom et al., Proc. Natl. Acad. Sci. USA, vol. 90, May 1993, pp. 4708-4712.
Yoshiro Kayanoki et al., J. Biochem., vol. 119, 1996, pp. 817-822.
Kristina E. Hill et al., Biomedical and Environmental Sciences, vol. 10, 1997, pp. 198-208.
G. Kohler et al., Nature, vol. 256, Aug. 7, 1975, pp. 495-497.
Sheryl M. Greenberg et al., Blood, vol. 72, No. 6, Dec. 1988, pp. 1968-1977.
Kristina E. Hill et al., Proc. Natl. Acad. Sci, USA, vol. 90, Jan. 1993, pp. 537-541.
D. E. Yelton et al., Curr Top Microbiol Immunol, vol. 81, pp. 1-7, 1978.
Katja Zurbonsen et al., European Journal of Pharmacology, vol. 320, pp. 215-221, 1997.
Rafferty et al. (Biochem J May 15, 1998; 332 (Pt1):231-6).
Dermer (Bio/Tehcnology, 1994, 12:320).
Burgess et al, J of Cell Bio. 111:2129-2138, 1990.
Lazar et al., Molecular and Cellular Biology 8:1247-1252, 1988.
Bowie et al. Science, 247:1306-1310, 1990, p. 1306, col. 2.
Freshney (Culture of Animal Cell, A Manual of Basic Technique, Alan R. Liss, Inc., 1983, New York, p4).
Jun Yan et al.; the Journal of Neuroscience, vol. 18, No. 21, pp. 8682-8691 (Nov. 1,1998).

* cited by examiner

*Primary Examiner*—Christopher H Yaen
(74) *Attorney, Agent, or Firm*—Birch, Stewart, Kolasch & Birch, LLP

(57) ABSTRACT

The present invention provides a peptide fragment or a series of peptide fragments having a cell death-inhibitory activity, having the amino acid sequence consisting of 103 amino acid residues at the C-terminal of selenoprotein P, or having said amino acid sequence with one or several amino acid residues therein being deleted, substituted or added, or having a partial sequence of either of the above amino acid sequences, a medicament for treatment comprising said peptide fragment or a series of peptide fragments, an antibody to said peptide fragment or a series of peptide fragments, and a method for screening a cell death-inhibitory activity using said peptide fragment or a series of peptide fragments. The preferable peptide fragment or a series of peptide fragments of the present invention has the amino acid sequences shown in SEQ ID NO: 1 and/or SEQ ID NO: 2 or has a partial sequence thereof.

4 Claims, 10 Drawing Sheets

Silver staining

Pattern of Non-Reductive SDS-PAGE of Purified
Selenoprotein P Fragments Applied in Varied Amounts 1. Glutathione Reductase (GR)
2. Glutathione S Transferase (GST)
3. Glutathione Peroxidase (GPX)
4. Superoxide Dismutase (SOD)
5. Selenoprotein P Fragment (selp)

|  | Activity |
|---|---|
| GR | 0 |
| GST | 0 |
| GPX | 100 |
| SOD | 200 |
| selp | 25600 |

SEQUENCE LISTING

<160> NUMBER OF SEQ ID NOS: 7

<210> SEQ ID NO 1
<211> LENGTH: 29
<212> TYPE: PRT
<213> ORGANISM: Human plasma
<220> FEATURE:
<221> NAME/KEY: misc_feature
<222> LOCATION: (1)..(29)
<223> OTHER INFORMATION: Xaa represents selenocysteine

<400> SEQUENCE: 1

Lys Arg Cys Ile Asn Gln Leu Leu Cys Lys Leu Pro Thr Asp Ser Glu
1               5                   10                  15

Leu Ala Pro Arg Ser Xaa Cys Cys His Cys Arg His Leu
            20                  25

<210> SEQ ID NO 2
<211> LENGTH: 28
<212> TYPE: PRT
<213> ORGANISM: Human plasma
<220> FEATURE:
<221> NAME/KEY: misc_feature
<222> LOCATION: (1)..(28)
<223> OTHER INFORMATION: Xaa represents selenocysteine

<400> SEQUENCE: 2

Thr Gly Ser Ala Ile Thr Xaa Gln Cys Lys Glu Asn Leu Pro Ser Leu
1               5                   10                  15

Cys Ser Xaa Gln Gly Leu Arg Ala Glu Glu Asn Ile
            20                  25

<210> SEQ ID NO 3
<211> LENGTH: 103
<212> TYPE: PRT
<213> ORGANISM: Human plasma
<220> FEATURE:
<221> NAME/KEY: misc_feature
<222> LOCATION: (1)..(103)
<223> OTHER INFORMATION: Xaa represents selenocysteine

<400> SEQUENCE: 3

Lys Arg Cys Ile Asn Gln Leu Leu Cys Lys Leu Pro Thr Asp Ser Glu
1               5                   10                  15

Leu Ala Pro Arg Ser Xaa Cys Cys His Cys Arg His Leu Ile Phe Glu
            20                  25                  30

Lys Thr Gly Ser Ala Ile Thr Xaa Gln Cys Lys Glu Asn Leu Pro Ser
        35                  40                  45

Leu Cys Ser Xaa Gln Gly Leu Arg Ala Glu Glu Asn Ile Thr Glu Ser
    50                  55                  60

Cys Gln Xaa Arg Leu Pro Pro Ala Ala Xaa Gln Ile Ser Gln Gln Leu
65                  70                  75                  80

Ile Pro Thr Glu Ala Ser Ala Ser Xaa Arg Xaa Lys Asn Gln Ala Lys
                85                  90                  95

Lys Xaa Glu Xaa Pro Ser Asn
            100

<210> SEQ ID NO 4
<211> LENGTH: 20
<212> TYPE: PRT
<213> ORGANISM: Human plasma

```
<400> SEQUENCE: 4

Lys Arg Cys Ile Asn Gln Leu Leu Cys Lys Leu Pro Thr Asp Ser Glu
1               5                   10                  15

Leu Ala Pro Arg
            20

<210> SEQ ID NO 5
<211> LENGTH: 21
<212> TYPE: PRT
<213> ORGANISM: Human plasma

<400> SEQUENCE: 5

Lys Arg Cys Ile Asn Gln Leu Leu Cys Lys Leu Pro Thr Asp Ser Glu
1               5                   10                  15

Leu Ala Pro Arg Ser
            20

<210> SEQ ID NO 6
<211> LENGTH: 381
<212> TYPE: PRT
<213> ORGANISM: Human plasma
<220> FEATURE:
<221> NAME/KEY: misc_feature
<222> LOCATION: (1)..(381)
<223> OTHER INFORMATION: Xaa represents selenocysteine
<220> FEATURE:
<221> NAME/KEY: SIGNAL
<222> LOCATION: (1)..(19)
<223> OTHER INFORMATION: Signal sequence

<400> SEQUENCE: 6

Met Trp Arg Ser Leu Gly Leu Ala Leu Ala Leu Cys Leu Leu Pro Ser
1               5                   10                  15

Gly Gly Thr Glu Ser Gln Asp Gln Ser Ser Leu Cys Lys Gln Pro Pro
            20                  25                  30

Ala Trp Ser Ile Arg Asp Gln Asp Pro Met Leu Asn Ser Asn Gly Ser
        35                  40                  45

Val Thr Val Val Ala Leu Leu Gln Ala Ser Xaa Tyr Leu Cys Ile Ile
50                  55                  60

Glu Ala Ser Lys Leu Glu Asp Leu Arg Val Lys Leu Lys Lys Glu Gly
65                  70                  75                  80

Tyr Ser Asn Ile Ser Tyr Ile Val Val Asn His Gln Gly Ile Ser Ser
                85                  90                  95

Arg Leu Lys Tyr Thr His Leu Lys Asn Lys Val Ser Glu His Ile Pro
            100                 105                 110

Val Tyr Gln Gln Glu Glu Asn Gln Thr Asp Val Trp Thr Leu Leu Asn
        115                 120                 125

Gly Ser Lys Asp Asp Phe Leu Ile Tyr Asp Arg Cys Gly Arg Leu Val
    130                 135                 140

Tyr His Leu Gly Leu Pro Phe Ser Phe Leu Thr Phe Pro Tyr Val Glu
145                 150                 155                 160

Glu Ala Ile Lys Ile Ala Tyr Cys Glu Lys Lys Cys Gly Asn Cys Ser
                165                 170                 175

Leu Thr Thr Leu Lys Asp Glu Asp Phe Cys Lys Arg Val Ser Leu Ala
            180                 185                 190

Thr Val Asp Lys Thr Val Glu Thr Pro Ser Pro His Tyr His His Glu
        195                 200                 205

His His His Asn His Gly His Gln His Leu Gly Ser Ser Glu Leu Ser
    210                 215                 220
```

```
-continued

Glu Asn Gln Gln Pro Gly Ala Pro Asn Ala Pro Thr His Pro Ala Pro
225                 230                 235                 240

Pro Gly Leu His His His Lys His Lys Gly Gln His Arg Gln Gly
                245                 250                 255

His Pro Glu Asn Arg Asp Met Pro Ala Ser Glu Asp Leu Gln Asp Leu
                260                 265                 270

Gln Lys Lys Leu Cys Arg Lys Arg Cys Ile Asn Gln Leu Leu Cys Lys
            275                 280                 285

Leu Pro Thr Asp Ser Glu Leu Ala Pro Arg Ser Xaa Cys Cys His Cys
        290                 295                 300

Arg His Leu Ile Phe Glu Lys Thr Gly Ser Ala Ile Thr Xaa Gln Cys
305                 310                 315                 320

Lys Glu Asn Leu Pro Ser Leu Cys Ser Xaa Gln Gly Leu Arg Ala Glu
                325                 330                 335

Glu Asn Ile Thr Glu Ser Cys Gln Xaa Arg Leu Pro Pro Ala Ala Xaa
                340                 345                 350

Gln Ile Ser Gln Gln Leu Ile Pro Thr Glu Ala Ser Ala Ser Xaa Arg
            355                 360                 365

Xaa Lys Asn Gln Ala Lys Lys Xaa Glu Xaa Pro Ser Asn
    370                 375                 380

<210> SEQ ID NO 7
<211> LENGTH: 20
<212> TYPE: PRT
<213> ORGANISM: Human plasma
<220> FEATURE:
<221> NAME/KEY: misc_feature
<222> LOCATION: (1)..(20)
<223> OTHER INFORMATION: Xaa represents selenocysteine

<400> SEQUENCE: 7

Thr Gly Ser Ala Ile Thr Xaa Gln Cys Lys Glu Asn Leu Pro Ser Leu
1               5                   10                  15

Cys Ser Xaa Gln
            20
```

ANTIBODIES TO PEPTIDE FRAGMENTS HAVING CELL DEATH-INHIBITORY ACTIVITY

This application is a Divisional of application Ser. No. 09/856,199 filed on May 18, 2001, now U.S. Pat. No. 7,199,097 and for which priority is claimed under 35 U.S.C. § 120. Application Ser. No. 09/856,199 is the national phase of PCT International Application No. PCT/JP99/06322 filed on Nov. 12, 1999 under 35 U.S.C. § 371. This application also claims priority of application Ser. No. 347863/1998 filed in Japan on Nov. 19, 1998 under 35 U.S.C. § 119. The entire contents of each of the above-identified applications are hereby incorporated by reference.

The present invention relates to a protein having a novel function. Specifically, the present invention relates to a peptide fragment or a series of peptide fragments having a cell death-inhibitory activity, a process for purifying said fragments, and an antibody to said peptide fragment or a series of peptide fragments. More specifically, the present invention relates to a peptide fragment or a series of peptide fragments that can be used as a medicament for protecting from exacerbation of conditions of, preventing or treating various diseases such as diseases related to cell death, or as an additive allowing for production of useful material by inhibiting cell death in cell culture, and an antibody to said peptide fragments or a series of peptide fragments.

BACKGROUND ART

It has been suggested that cell death not only plays an important role in basic control of the nervous system, the endocrine system and the immune system in higher organisms but also is deeply involved in many diseases (Thompson C. B., Science, vol. 267, p. 1456-1462 (1995). Some diseases including, for example, autoimmune diseases such as systemic lupus erythematosus, neurodegenerative diseases due to death of neurons, organ transplantation injuries associated with organ transplantation, etc. may be regarded as one due to influence of cell death where apoptosis is involved.

Factors causing cell death includes both an extraneous factor and an intrinsic factor. For an extraneous factor, those of which substantial existence as substance accelerating cell death have been established include TNF involved in the immune system (Zheng, L., et al., Nature, vol. 377, p. 348-351 (1995)), Fas ligand (Suda T., et al., Cell, vol. 75, p. 1169-1178 (1993)), glucocorticoids (Wyllie A. H., Nature, vol. 284, p. 555-556 (1980)), etc. An extraneous factor also includes lack of a growth factor indispensable to cell growth, such as erythropoietin, interleukins, nerve growth factor, or lack of nutritional factors. In these cases, cell death is induced by apoptosis caused by change in physiological conditions. Apoptosis may also be induced by non-physiological stresses such as radiation, temperature, anticancer agents, calcium ionophore, active oxygen, etc. In addition, necrosis may also be induced by burn, toxic substance, ischemia, attack by complements, infection with virulent virus, administration of overdose medicaments or overdose radiation.

For an intrinsic factor, there are changes in the metabolic system such as intracellular concentration of $Ca^{2+}$, metabolism of nucleic acids, metabolism of amino acids, metabolism of energy, etc., which lead to cell death. Control of these apoptotic signals could have lead to protection from exacerbation of conditions of, prevention or treatment of various diseases. However, at present, the mechanism is not so simple that mere control of the causal substance and factors that have hitherto been established cannot afford sufficient clinical application.

On the other hand, as substance that have hitherto been proved to inhibit cell death, intracellular factors such as bcl-2 and bcl-x are known that are believed to inhibit most of apoptotic signals (Boise L. H., et al., Cell, vol. 74, p. 597-608 (1993)). However, these agents must intracellularly be expressed for causing inhibition of cell death and effects can hardly be obtained by extracellular addition of these agents. Extracellular factors for inhibiting cell death have also been reported that inhibit apoptosis by active oxygen, including superoxide dismutase (hereinafter also referred to as "SOD") (Greenlund L. J., et al., Neuron, vol. 14, p. 303-315 (1995)), catalase (Sandstrom P. A. and Buttke T. M., Proc. Natl. Acad. Sci. USA, vol. 90, p. 4708-4712 (1993)), and glutathione peroxidase (Kayanoki Y., et al., J. Biochem., vol. 119, p. 817-822 (1996)). However, cell death cannot effectively be inhibited by these extracellular factors alone.

While culturing cells, cell death is induced due to stress to cells imposed by substances from the cultured cells per se or from extraneous additives. However, it is not all the cells that are put to death under certain conditions. For those cells that survived the circumstances, proteins necessary for suppressing the cell death-inducing signals due to stress under their thresholds should have already been expressed, or newly induced, either intracellularly or extracellularly. Such proteins include, as envisaged, transcription factor, synthases, enzymes related to metabolism, oxidases, reductases, kinases, transferases, apoptosis-inhibiting proteins, etc. That is, sensitivity to stress in each of respective cells may vary due to difference in their expression level of these proteins. Thus, even if the mechanisms of cell death are not always the same, if the cell death-inducing signals could be suppressed under their thresholds by extraneously adding an inhibitory agent to cell death due to certain stress, then cell death could possibly be inhibited not only in cultured cells but also within the living body where similar stress occurred.

Moreover, cell death is closely related to diseases. Thus, identification of a number of agents having a cell death-inhibitory activity within the living body to control a variety of cell deaths would not only allow for clinical application such as treatment of diseases but also for application to effective culture of cultured cells. Indeed, although some factors are known that inhibit cell death, e.g. bcl-2, bcl-x, etc. as intracellular cell death-inhibitory factors, or SOD, catalase, glutathione peroxidase, etc., as extracellular factors, it is difficult to inhibit cell death in all types of cells by extracellular addition of these factors. This is due to difference in processes through which cell death is mediated based on difference in their mechanisms. Taking this into consideration, there is a need to identify activities that significantly, and more specifically, inhibit a variety of cell deaths. That is, for those cell deaths that are not subject to inhibition by known materials, there is a need to searching for factors that can significantly inhibit said cell deaths. In addition, cell death-inhibitory factors are likely to be present for maintaining homeostasis within the living body and hence identification of such factors is extremely significant.

While culturing cells under cell-free conditions or another special conditions, apoptosis induced by stress is frequently observed. Cell culture is performed under these cell death-inducing conditions and with the index of the cell death-inhibitory activities effective components in blood may be purified by using various chromatographies to thereby prepare proteinaceous components that inhibit cell death.

DISCLOSURE OF INVENTION

As a result of thorough investigation, it was found that a peptide fragment or a series of peptide fragments derived from said peptide fragment has an excellent cell death-inhibitory activity, said peptide fragment having the amino acid sequence consisting of 103 amino acid residues at the C-terminal of selenoprotein P, or having said amino acid sequence with one or several amino acid residues therein being deleted, substituted or added, or having a partial sequence of either of the above amino acid sequences. The term "a series of peptide fragments" as used herein refers to a group of peptide fragments with different minute structures due to presence or absence of glycosylation, difference in electric charge, diversity in fragmentation, etc.

Particularly preferable series of peptide fragments according to the present invention have the amino acid sequences of the formula (I):

Lys Arg Cys Ile Asn Gln Leu Leu Cys Lys Leu Pro Thr Asp Ser Glu Leu Ala Pro Arg Ser Xaa Cys Cys His Cys Arg His Leu (SEQ ID NO: 1) and/or the formula (II):

Thr Gly Ser Ala Ile Thr Xaa Gln Cys Lys Glu Asn Leu Pro Ser Leu Cys Ser Xaa Gln Gly Leu Arg Ala Glu Glu Asn Ile (SEQ ID NO: 2)

wherein Xaa represents selenocysteine, or a partial sequence of these amino acid sequences.

Moreover, findings during their purification procedure revealed that said peptide fragment or a series of peptide fragments (a) are recovered in fractions of molecular weight 10 kDa to 30 kDa by molecular size fractionation with membrane; (b) have structures showing isoelectric points at between pH 7 and pH 8 and at pH 8 or more in blood as a result of testing of binding to an ion exchange resin; (c) show two bands at molecular weight 13 to 14 kDa and two bands at 16 to 17 kDa as a glycosylated form of the former bands in non-reductive SDS-PAGE; and (d) in addition to the bands as described above, have a band pattern of 3 to 4 kDa, 7 to 9 kDa and 10 to 12 kDa SDS-PAGE under reductive condition, and that said peptide fragment exhibits the activity even after further fragmentation.

BEST MODE FOR CARRYING OUT THE INVENTION

Figure 1:
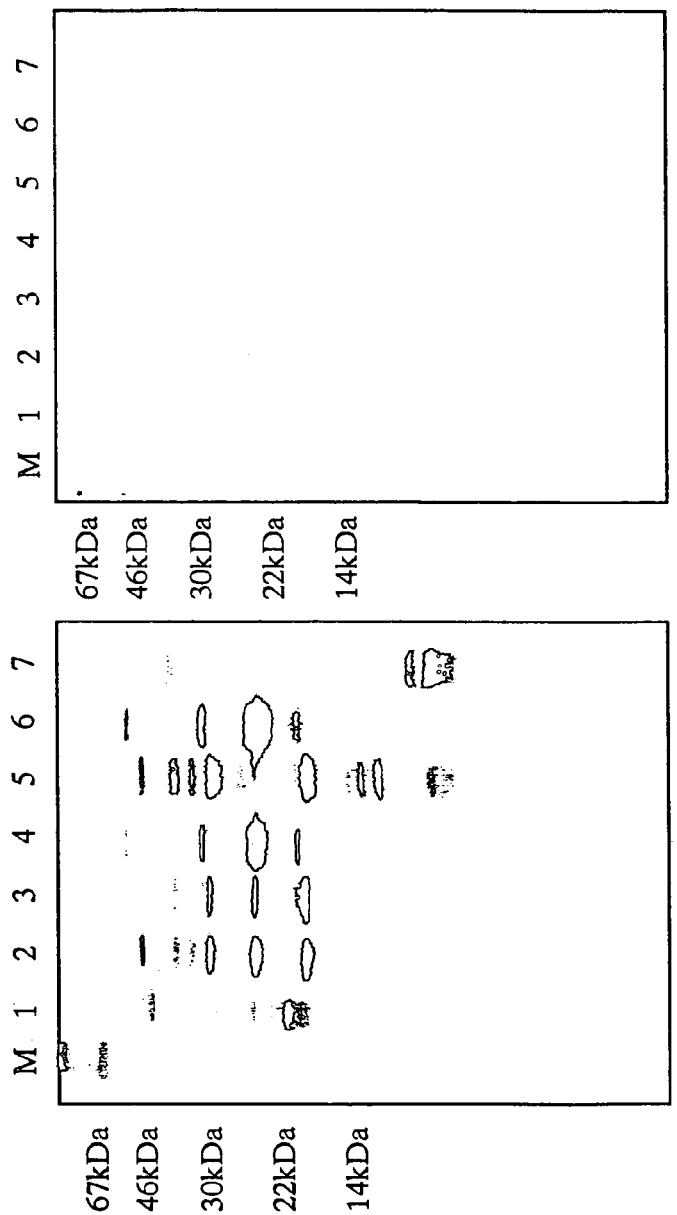
FIG. 1 shows electrophoretograms either with silver staining or Western blotting at various stages of purification of the peptide fragment or a series of peptide fragments having a cell death-inhibitory activity of the present invention.

For screening factors having the cell death-inhibitory activity, a culture system needs to be established where cell death is induced. As one of preferable embodiments in the present invention, a culture system of Dami cells, human megakaryoblasts, with serum free culture medium supplemented with albumin was used for screening. Dami cells may be subcultured on a mixed culture medium of RPMI 1640, D-MEM and F-12 (1:2:2) supplemented with 0.1% BSA and 0.05 μM 2-mercaptoethanol but can hardly grow on albumin-deprived medium. With culture medium containing 0.01 to 0.5% human serum albumin, the cells grow normally but are put to death on Day 4 abruptly not gradually. A diluted sample of active fractions may be added to this culture system to thereby estimate the cell death-inhibitory activity.

Although Dami cells might be most effectively used for assay, the present invention is not limited to Dami cells but any type of cells can be utilized for screening the cell death-inhibitory activity insofar as cell death is induced under the similar conditions. Other applicable cell types include, for example, CEM, Molt4, etc. For albumin used in this assay system, any albumin may be used insofar as cell death is observable. By way of example, human serum albumin F-V (manufactured by SIGMA) may preferably be used.

Based on the assay system as described above, the present inventors have aimed at components within the living body, especially those derived from blood, and thoroughly investigated for searching the activity of interest. As a result, the present inventors have found a desired activity in plasma or serum from mammals, typically human beings. Fractions with detected cell death-inhibitory activity exhibited the activity up to 1600-folds to 3200-folds dilution in case of plasma or serum from human source or the activity not more than 100-folds dilution in case of fetal calf serum. For the purpose of quantification of the cell death-inhibitory activity as used herein, dilution of not more than 100-folds is indicated as "0" while in case of dilution of more than 100-folds, a figure of said dilution per se is used for indicating the activity.

A series of peptide fragments, provided as active substance according to the present invention, are rather stable to heat, a denaturing agent, a broad range of pH or protease in blood as compared to common enzymes and hence can be purified by using a wide variety of purification procedures. Thus, fractionations with applicable various carriers may be used such as various chromatographic procedures including heparin chromatography, cation exchange chromatography, anion exchange chromatography, hydrophobic chromatography, gel filtration chromatography, reverse phase chromatography, hydroxyapatite chromatography, etc. In addition to these, other various fractionations may also be applicable such as ammonium sulfate precipitation, molecular size fractionation with membrane, isoelectric focusing, electrophoretic fractionation, etc. These fractionations may suitably be used in combination to effectively fractionate the desired cell death-inhibitory activity. One of preferable combinations is shown in Example 2. Briefly, in the order of manipulation, it includes heparin chromatography, ammonium sulfate precipitation, anion exchange chromatography, cation exchange chromatography, hydrophobic chromatography, heparin chromatography, gel filtration chromatography, reverse phase chromatography and anion exchange chromatography.

This combination of purification procedures can afford active fraction of such purity as having not more than 5% estimated impurities, for example, with the activity of $2 \times 10^5/1$ mg protein/ml starting from human plasma as a source. In view of the activity of starting plasma being about 20 to 40/1 mg protein/ml, it is estimated that specific activity was increased by about 5,000 to 10,000 times.

The components having the cell death-inhibitory activity from plasma according to the present invention purified and identified as described above are characterized by the following properties.

Heparin Binding

The components having the cell death-inhibitory activity are tested for their binding capability to heparin and it is revealed that the components bind to heparin weakly. This finding suggests that the components having the cell death-inhibitory activity according to the present invention are relatively charged positive. Thus, it is estimated that the components are possibly involved in protection of cellular surface by binding with heparan sulfate on the surface of cells such as erythrocytes or the vascular endothelial cells easily subject to stress in blood.

Distribution of Activity by Molecular Size Fractionation with Membrane

For heparin-binding fractions from plasma, the cell death-inhibitory activity is concentrated with membranes of fractionating molecular weights 10 kDa, 30 kDa and 50 kDa to recover 90 to 95% activity for 10 kDa, 10 to 20% for 30 kDa and 0 to 10% for 50 kDa. Thus, 80 to 90% of the components having the cell death-inhibitory activity according to the present invention has a molecular weight of 10 kDa to 30 kDa in the presence of other heparin-binding proteins. However, some of the components having the activity have a molecular weight of more than that range, suggesting that there exist other active substances with different molecular weights due to modification, polymerization or difference in processing.

Fractionation with Ammonium Sulfate

For a sample of crude fractionation, all the active components are precipitated with about 2 M ammonium sulfate. More strictly speaking, however, addition of about 3 M ammonium sulfate is necessary for precipitating all the active components. The active components of the present invention are rather poorly salted-out although they may occasionally co-precipitate with some other proteins while salting out.

Binding to Ion Exchange Resin

With a suitable buffer of about 20 mM, the active components partially bind to an anion exchanger at pH 8.0 or more but it is not all the active components that bind. On the other hand, the active components also bind to a cation exchanger at pH 7.0 or less. Thus, it is estimated that the active components of the present invention have both structures having isoelectric point at between pH 7 and 8 and having isoelectric point at pH 8 or more in blood.

Fractionation with Hydrophobic Chromatography

With Macro-Prep Methyl HIC or Macro-Prep t-butyl HIC carrier, adsorption of the active fractions is hardly observed in the presence of 20 mM Tris, pH 8.0, 200 mM NaCl and 1.2 M ammonium sulfate. When a concentration of ammonium sulfate is increased to 1.5 M, however, 30 to 50% of the active fractions are adsorbed. If a concentration of ammonium sulfate is increased up to 2 to 2.4 M, almost all the active fractions may be adsorbed. With another carriers, it is possible to purify efficiently the active components of the present invention under the similar conditions.

Fractionation with Gel Filtration

When the heparin-binding fractions are further fractionated by using gel filtration chromatography, almost all the activity is recovered in fractions of size 30 kDa to 40 kDa of molecular weight. On the contrary, the active components of the present invention, as actually obtained, have a molecular weight of 30 kDa or less in electrophoresis. Thus, it is estimated that the active components of the present invention are likely to bind to other molecules.

PAGE (Polyacrylamide Gel Electrophoresis)

Fractionation of the active components of the present invention with PAGE under non-denaturing condition does not render the activity being converged to a single band. It is thus estimated that the active components of the present invention are not represented by a single structure but exist in various forms with different molecular weights due to formation of dimer, difference in charge, glycosylation or various types of fragmentation of the peptide fragments consisting of the active components of the present invention. It is demonstrated in SDS-PAGE under non-reductive condition that the active components are consisted of peptides showing two bands of molecular weight about 13 to 14 kDa and two bands of about 16 to 17 kDa, the latter being a glycosylated form of the former. Under reductive condition, bands of about 3 to 4 kDa, about 7 to 9 kDa and about 10 to 12 kDa also occur in addition to the above bands. This suggests that there are peptides having S—S bonds therein corresponding to the bands of about 13 to 14 kDa and of about 16 to 17 kDa, wherein some of the peptides are internally cleaved, and reduction cleaves the S—S bonds to produce peptides of the above additional sizes. This is supported by the fact that an antibody directed to the peptide fragment of about 3 to 4 kDa is reactive with all the peptide fragments other than those of about 7 to 9 kDa and of about 10 to 12 kDa. Moreover, since the peptide fragment per se of about 3 to 4 kDa obtained under reductive condition still has the cell death-inhibitory activity, it is highly possible that this peptide fragment comprises a region deeply concerned with the activity.

Analysis of N-Terminal Amino Acid Sequence

It was found that the peptide fragments identified in the above PAGE had high homology to the amino acid sequence consisting of 103 amino acid residues at the C-terminal of human selenoprotein P as estimated from cDNA of human selenoprotein P.

The N-terminal amino acid sequence was analyzed and, as a result, it was found that the peptide fragment having the cell death-inhibitory activity of the present invention or a series of peptide fragments derived from said peptide fragment had as a basic unit (1) a peptide having the amino acid sequence: Lys Arg Cys Ile Asn Gln Leu Leu Cys Lys Leu Pro Thr Asp Ser Glu Leu Ala Pro Arg Ser Xaa Cys Cys His Cys Arg His Leu (SEQ ID NO: 1), starting from the 260th Lys in human selenoprotein P, and (2) a peptide having the amino acid sequence: Thr Gly Ser Ala Ile Thr Xaa Gln Cys Lys Glu Asn Lys Pro Ser Leu Cys Ser Xaa Gln Gys Leu Arg Ala Glu Glu Asn Ile (SEQ ID NO: 2) wherein Xaa is selenocysteine, starting from the 293rd Thr in human selenoprotein P.

The active components of the present invention are present as a conjugate or a complex of the above constituting units, i.e. the peptide fragments, and exert the cell death-inhibitory activity. Each of the respective constituting units has also the activity. There also exist diverse molecular species due to the presence or absence of glycosylation, difference in charge, difference in fragmentation, especially diversity of the peptide fragments at the C-terminal end. Even in a mixture of such diverse molecular species, the cell death-inhibitory activity of the present invention is exhibited. Therefore, the active components of the present invention encompass not only each of the individual peptide fragments having the activity or partial fragments thereof but also a group of the diverse peptide fragments, i.e. a series of peptide fragments, as a whole, insofar as the cell death-inhibitory activity is exerted.

It has not been reported that there are processed forms of selenoprotein P with the sizes as in the present invention and much less that suggests such fragments alone have the activity.

Selenoprotein P was identified in 1977 as another selenium-containing protein other than glutathione-peroxidase. In 1982, it was revealed that selenium was incorporated into said protein in the form of selenocysteine. In 1991, a full-length amino acid sequence of selenoprotein P was determined by cloning selenoprotein P cDNA and, as a result, possibility that said protein contains at most ten selenocysteine residues was demonstrated (Hill K. E. and Burk R. F., Biomed. Environ. Sci., 10, p. 198-208 (1997)). However, there have been no attempt to perform expression of a recombinant protein, or to identify amino acid sequences corresponding to the active peptide fragment or a series of the peptide fragments of the present invention in purified selenoprotein P, or to identify the active site. There is a report that human selenoprotein P was purified with anti-selenoprotein P antibody. However, the antibody used therein recognized the amino acid sequence at the N-terminal of selenoprotein P and hence cannot be used for purifying the peptide fragment in accordance with the present invention. Therefore, the instant application is the first to estimate the activity of the active peptide fragment or a series of the active peptide fragments as characterized herein.

The activity of selenoprotein P has been reported including an antioxidant activity due to the presence of selenium and glutathione peroxidase activity. Up till the present, however, there is no report that the peptide fragment or a series of peptide fragments obtained in accordance with the present invention are indeed present within the living body and exhibit the excellent activity. Of course, the presence of the activity as characterized herein has not been reported.

Comparison of Activity with Other Proteins

Other than the peptide fragment or a series of peptide fragments having the cell death-inhibitory activity of the present invention, selenoproteins and related proteins with an antioxidant activity are examined whether they exhibit the cell death-inhibitory activity in Dami cells. As a result, the activity is somewhat observed only in glutathione peroxidase and SOD. However, in comparison with the peptide fragment or a series of peptide fragments having the cell death-inhibitory activity of the present invention, the activity is as low as 1/100 or less of that of the present invention, which may be regarded as substantially no activity. Then, compared with a full-length selenoprotein P, most relevant to the active components of the present invention, marked predominance of the active components of the present invention, fragmented product of selenoprotein P, is observed for the cell death-inhibitory activity and hence significance of "fragmentation" is demonstrated. That is, the active components of the present invention as characterized herein are the only proteins having the cell death-inhibitory activity in blood that are not hitherto known. Therefore, identifying the presence of the active components has great significance.

It is also possible to design chemically synthesized compounds, based on the above finding, by utilizing the peptide fragment provided in accordance with the present invention as a leading substance.

Using the peptide fragment having the cell death-inhibitory activity of the present invention as an immunogen, an antibody may be obtained that recognizes and binds to said novel peptide fragment. Although any material containing the peptide fragment or a series of peptide fragments of the present invention may serve as an immunogen, the fraction prepared in Example 2 may preferably be used. The peptide fragment of the present invention or a portion thereof may also be used as an immunogen that is prepared by using a peptide synthesizer or produced from microorganisms such as *E. coli* or yeast with the genetic recombination technique. Also, an expression plasmid for animal cell in which a gene encoding the peptide fragment of the present invention or a portion thereof is incorporated may be used as a DNA vaccine for an immunogen.

Such a peptide fragment for use as an immunogen preferably has, but is not limited to, the amino acid sequence: Lys Arg Cys Ile Asn Gln Leu Leu Cys Lys Leu Pro Thr Asp Ser Glu Leu Ala Pro Arg Ser Xaa Cys Cys His Cys Arg His Leu Ile Phe Glu Lys Thr Gly Ser Ala Ile Thr Xaa Gln Cys Lys Glu Asn Leu Pro Ser Leu Cys Ser Xaa Gln Gly Leu Arg Ala Glu Glu Asn Ile Thr Glu Ser Cys Gln Xaa Arg Leu Pro Pro Ala Ala Xaa Gln Ile Ser Gln Gln Leu Ile Pro Thr Glu Ala Ser Ala Ser Xaa Arg Xaa Lys Asn Gln Ala Lys Lys Xaa Glu Xaa Pro Ser Asn, wherein Xaa is selenocysteine (SEQ ID NO: 3), or the amino acid sequence: Lys Arg Cys Ile Asn Gln Leu Leu Cys Lys Leu Pro Thr Asp Ser Glu Leu Ala Pro Arg (SEQ ID NO: 4).

Although any mammals may be used for immunization, rabbit is preferably used for obtaining antiserum and mouse is preferred if a monoclonal antibody is prepared by the cell fusion technique as described below. Age of animals may be, for example, 5 to 10 weeks in case of mouse. Both male and female animals may be used. An antigen for immunization may be used, for example, as a suspension in an appropriate adjuvant or as a solution in a physiological saline, which is then administered to animals intraperitoneally, subcutaneously or intravenously. This immunization is performed once to five times at the interval of 2 to 3 weeks. The final immunization is made, for example, by suspending the antigen for immunization in physiological saline and intravenously administering the suspension to animals. From the immunized animals, blood is drawn for preparing antiserum or spleen cells are prepared for obtaining hybridoma producing an antibody as described in Kohler G. and Milstein C., Nature, vol. 256, p. 495 (1975). In case of mouse, for example, spleen cells from the immunized mice are fused with mouse myeloma cells to produce hybridomas.

Any culture medium may be used that is suitable for culturing hybridomas. Commonly, RPMI 1640 or Eagle MEM, supplemented with 5 to 10% fetal calf serum, 3.5 to 4.0 g/l L-glutamine and antibiotics such as penicillin or streptomycin, is used. A serum free medium such as ASF 104 (manufactured by Ajinomoto K.K.) or CM-B (manufactured by Sanko Jun-yaku K.K.) may also be used. Among the hybridomas obtained, those producing a monoclonal antibody specific to the peptide fragment of the present invention are screened. Screening may be performed, for example, by sampling supernatants from the culture of hybridomas and examining whether they react with the peptide fragment of the present invention or a portion thereof, using the known techniques such as EIA, RIA or Western blotting. This procedure may also be applied for investigating whether an antibody titer is increased in the immunized animals.

INDUSTRIAL APPLICABILITY

It is reported that in general a free fatty acid level is raised by as much as more than three times to bring about cellular toxicity at the time when the living body is subject to a certain stress such as hemostasis, occurrence of inflammation, disorder in organs, damage in cells, damage in blood vessels, bacterial infection, viral infection, etc. ("Chemistry of Lipids", p. 170-179, ed. by Haruo Nakamura, Asakura Shoten (1990); "Handbook of Cerebral Apoplexy Experiment", p. 437-471, supervised by Keiji Sano, IPC (1990)). From this teaching, it is anticipated that cells are adversely effected by a fatty acid under circumstances where stressful state is maintained though sensitivity may vary depending on the types of cells. That is, against stress that may be encountered while operation, i.e. bleeding, hemostasis or ischemia, stress of reperfusion after ischemia associated with diseases or organ transplantation, or stress by continuous inflammation, the active peptide fragment or a series of peptide fragments of the present invention, derived from selenoprotein P, can reduce adverse effects by a fatty acid or prevent exacerbation of conditions by enhancing antioxidant activity of cells. The active peptide or a series of peptide fragments of the present invention would also serve as stabilizing cells by enhancing antioxidant ability of cells against any phenomena where oxidation stress of cells is raised through the similar mechanism.

It is anticipated that the active peptide fragment or a series of peptide fragments of the present invention function within the living body in the activated form after processing for protecting cells from stress-derived death and for stabilizing cells. That is, when too much stress is burdened to such a degree that the living body is no more durable thereto, cell death could have occurred. Thus, in such a case, if the active peptide fragment or a series of peptide fragments of the present invention could be supplied extraneously, it would be possible to prevent from progressing into severe diseases or to treat diseases. Diseases that can be prevented or treated by the active peptide fragment or a series of peptide fragments of the present invention include ones induced and effected by oxidation stress such as AIDS (acquired immunodeficiency syndrome), Parkinson's disease, Alzheimer's disease, etc. Since it is found that oxidized LDL is involved in onset of arteriosclerosis as a causing factor, application for protection from exacerbation of conditions, prevention or treatment of arteriosclerosis is also envisaged. It is also efficacious to diseases in which reperfusion injury is observed such as myocardial infarction, cerebral infarction or organ transplantation.

As for AIDS, close relationship between selenoproteins and AIDS or HIV (human immunodeficiency virus) has recently been reported. Briefly, it is reported that selenium level in serum is decreased with HIV infection and that decrease in selenium level is correlated with mortality or decrease in CD4 cells (Olmsted L. et al., Biol. Trace Elem. Res., vol. 20, p. 59-65, 1989; Allard J. P. et al., Am. J. Clin. Nutr., vol. 67, p. 143-147, 1998). It is also reported that a nucleic acid sequence of HIV comprises a sequence that encodes selenoproteins if frame-shifted and indeed, upon HIV infection, T lymphomas lose their ability to synthesize selenoproteins, antioxidant enzymes such as glutathione peroxidase (Taylor E. W. et al., Biol. Trace Elem. Res., vol. 56, p. 63-91, 1997; Gladyshev V. N. et al., Proc. Natl. Acad. Sci. USA, vol. 96, p. 835-839, 1999). It is also suggested that oxidation stress may be involved in cell death of T lymphocytes in AIDS (Romero-Alvira D. et al., Med. Hypotheses, vol. 51, p. 169-173, 1998).

Actually, selenium level in blood was determined and, as a result, it was found that the selenium level in blood in AIDS patients was as low as about half of healthy adults. It was suspected that selenoprotein P level in blood in AIDS patients might possibly be different from that of healthy adults. Thus, selenoprotein P level in plasma was determined in AIDS patients with EIA. As a result, it was observed that a selenoprotein P level tends to be higher in AIDS patients with less exacerbation of disease or with no onset of disease than in AIDS patients with prompt exacerbation of disease. Moreover, immunoprecipitation was performed with a carrier to which anti-selenoprotein P antibody is bound in order to compare the state of selenoprotein P in plasma between AIDS patients and healthy adults. As a result, it was demonstrated that AIDS patients with less exacerbated disease or with no onset of disease had the same pattern as healthy adults whereas AIDS patients with promptly exacerbated disease showed distinct pattern. From these results, possibility was suggested that selenoprotein P might be useful for arresting and preventing onset of AIDS.

Correlation between selenium level, especially selenoprotein P level, in blood and AIDS has been suggested as described above. However, that partial segments at the C-terminal of selenoprotein P having a particular amino acid sequence have the cell death-inhibitory activity significantly higher than that of selenoprotein P per se and thus are useful for prevention and treatment of AIDS has never known hitherto.

In addition, it is demonstrated that the active peptide fragment or a series of peptide fragments efficiently work in culture of B cells and T cells. Thus, they may also be used as an immunostimulatory or immunoregulatory agent through stabilization or regulation of cells of the immune system. Moreover, they may also be used for enhancing efficiency of culture conditions, for example, in case of production of useful biological substance by protecting cells from death due to excessive stress while cell culture.

The peptide fragment of the present invention or peptide fragments having a partial sequence thereof and an antibody capable of binding to said peptide fragment may be used in an antigen detection system such as Western blotting or ELISA and for preparing a diagnostic agent. The antibody of the present invention may be bound to an appropriate carrier which is used for affinity chromatography for purifying the peptide fragment having the activity of the present invention.

In addition, it is demonstrated that the active peptide fragment efficiently works in culture of B cells and T cells. A teaching that an antibody to the active peptide fragment of the present invention as an immunogen does affect B cells was also obtained at immunization with said active peptide fragment. Taken together these demonstration and teaching, the antibody of the present invention may also be used as an immunostimulatory or immunoregulatory agent through stabilization or regulation of cells of the immune system.

The present invention is explained in more detail by means of the following Examples wherein reagents were purchased from Wako Jun-yaku K.K., Takara Shuzo K.K., Toyobo K.K. and New England BioLabs unless otherwise instructed.

EXAMPLE 1

(Assay)

To 1 ml Dami cells (described in Greenberg S. M. et al., Blood, vol. 72, p. 1968-1977 (1988); $1 \times 10^6$ cells/dish/3 ml), which can be subcultured in serum free medium SFO3 (manufactured by Sanko Jun-yaku K.K.) containing 0.05 μM 2ME and 0.1% BSA, was added 2 ml 1:2:2 mixed medium (SA medium) of RPMI 1640/D-MEM/F-12. The cells were cultured for three days and recovered for assay. The cells were washed twice with 50% PBS/SA/0.03% HSA (manufactured by SIGMA) and suspended in the same medium at $3 \times 10^4$ cells/ml. The cell suspension was added to a 96-well plate in each 200 μl for wells for sample addition or in each 100 μl for wells for serial dilution. To the wells for sample addition was added 2 μl assay sample and, after stirring, a serial dilution was made with the wells containing 100 μl cell suspension. The plate was incubated at 37° C. in $CO_2$ incubator for 4 to 5 days followed by estimation.

For estimation, it was examined to what folds of dilution of tested samples the cells could survive in view of the fact that on Day 4 the cells in wells without the activity were put to death whereas the cells in wells with the activity survived.

EXAMPLE 2

(Purification of Components Having Cell Death-Inhibitory Activity)

In the following purification procedure, the activity was estimated in accordance with the assay procedure described in Example 1.

The cell death-inhibitory activity in plasma shows heparin-binding activity. Thus, fractionation with a heparin column was initially performed for collecting heparin-binding fractions from plasma. Using human plasma as starting material, heparin-binding proteins in plasma were adsorbed to a heparin column (Heparin Sepharose: manufactured by Pharmacia). After washing with 0.3 M sodium chloride, the adsorbed fractions were eluted with 2 M sodium chloride. Although most of the cell death-inhibitory activity of interest was recovered in the fractions after washing with 0.3 M sodium chloride, the fractions eluted with 2 M sodium chloride were used for purification of active substance.

For crude fractionation of the heparin-bound cell death-inhibitory activity, fractionation with ammonium sulfate precipitation was performed. To the heparin-binding fractions eluted with 2 M sodium chloride was added ammonium sulfate in an amount of 31.3% W/V (about 2 M) based on a total amount of the fractions and precipitates were recovered. The precipitates were dissolved in water and dialyzed against water with a dialysis membrane of M.W. 3,500 cut. After completion of dialysis, the solution was recovered and 1 M Tris-HCl buffer, pH 8.0 was added thereto in an amount of 1/50 volume based on a total of the solution. A concentration of the solution was adjusted with 20 mM Tris-HCl buffer, pH 8.0 so that 20 to 30 of OD280 value was obtained. The solution was filtrated with 1.0 μm and 0.45 μm filters for removal of impurities.

An anion exchange chromatography was performed by passing the proteinaceous solution after filtration through anion exchange chromatographic carrier (Macro-prep High Q: manufactured by BioRad) equilibrated with 20 mM Tris-HCl buffer, pH 8.0. The activity was detected in non-adsorbed fractions and fractions eluted with 50 mM sodium chloride, which were collected. To the active fractions obtained by anion exchange chromatography was added a 6:4 mixture of 1 M citrate buffer, pH 4.0 and 1 M citric acid in an amount of 1/50 volume based on a total of the fractions so that a proteinaceous solution was obtained as 20 mM citrate buffer, pH about 4.0.

A cation exchange chromatography was performed by passing the proteinaceous solution through cation exchange chromatographic carrier (Macro-prep High S: manufactured by BioRad) equilibrated with 20 mM citrate buffer, pH 4.0. The column was washed with 20 mM citrate buffer, pH 4.0 containing 220 mM sodium chloride. The activity was detected in fractions eluted with 20 mM citrate buffer, pH 4.0 containing 550 mM sodium chloride, which were collected.

To the fractions eluted with 550 mM sodium chloride was added 1 M Tris-Aminomethane solution in an amount of 1/30 volume based on a total of the fractions and pH was adjusted to about 7.5. To this solution was added a 3.5 M ammonium sulfate solution (pH was adjusted to about 7.5 by adding 1 M Tris-HCl buffer, pH 8.5 in an amount of 1/50 volume) in an amount of 2/3 volume. Then, a salt concentration was adjusted so that 1.4 M ammonium sulfate and 330 mM sodium chloride concentrations were obtained. The solution was filtrated with 0.45 μm filter for removal of impurities.

A hydrophobic chromatography was performed by passing the proteinaceous solution after filtration through hydrophobic chromatographic carrier (Macro-prep Methyl HIC: manufactured by BioRad) equilibrated with 20 mM Tris-HCl buffer, pH 7.5 containing 1.4 M ammonium sulfate and 330 mM sodium chloride. The activity was detected in non-adsorbed fractions and fractions eluted with the buffer for equilibration, pH 7.5, which were collected. The activity could hardly be detected in the adsorbed fractions. For the purpose of rendering the active fractions be adsorbed onto the hydrophobic chromatographic carrier, to the active fractions was added the 3.5 M ammonium sulfate solution, pH about 7.5 so that 2.0 M of an ammonium sulfate concentration was obtained. The sample was passed through hydrophobic chromatographic carrier (Macro-prep Methyl HIC: manufactured by BioRad) equilibrated with 20 mM Tris-HCl buffer, pH 7.5 containing 2.0 M ammonium sulfate and 240 mM sodium chloride to render the active components be adsorbed. After washing with the buffer for equilibration, the adsorbed active components were eluted with 20 mM Tris-HCl buffer, pH 8.0. The recovered active fractions were dialyzed against water overnight. For ensuring adsorption of the active fractions onto heparin column, 1 M citrate buffer, pH 4.5 was added to the recovered active fractions in an amount of 1/50 volume to adjust pH about 5.0. Up to this procedure, see FIG. 1.

A 20 mM phosphate buffer, pH 6.5 ("Buffer A") and a 20 mM phosphate buffer, pH 6.2 containing 2 M sodium chloride ("Buffer B") were prepared. The pH adjusted, active fractions were passed through heparin column (Hi-Trap Heparin: manufactured by Pharmacia) equilibrated with Buffer A. The column was washed with a twice volume of a 5% mixture of Buffer B in Buffer A (0.1 M NaCl). The active fraction was eluted with a 20% mixture of Buffer B in Buffer A (0.4 M NaCl) and recovered. The thus obtained active fraction was concentrated to about 15 mg/ml with a membrane concentrator (Centriprep 3: manufactured by Amicon). To the concentrated active fraction was added 2% acetic acid based on a total of the fraction and then impurities were removed with 0.45 µm filter.

Gel filtration chromatography was performed by passing 1 ml of the active fraction through gel filtration chromatographic carrier (Superdex 200 pg: manufactured by Pharmacia) equilibrated with a solution containing 2% acetic acid and 500 mM sodium chloride. After fractionation, the active fraction was recovered.

The above fraction was passed through C4 reverse phase HPLC (Wakosil 5C4-200: 6 mm×150 mm: manufactured by Wako Jun-yaku K.K.) equilibrated with 1% acetonitrile containing 0.1% trifluoroacetic acid and 1% isopropanol. The column was washed with the buffer used for equilibration. A linear gradient elution with 1% to 40% acetonitrile containing 0.1% trifluoroacetic acid and 1% isopropanol was then performed and the obtained active fractions were recovered. The progress of the activity and the specific activity obtained in each of the above purification procedures is summarized in Table 1 below.

TABLE 1

| Purification Step | Conc. of Protein (mg/ml) | Activity | Specific Activity |
|---|---|---|---|
| (1) | 64 | 2400 | 38 |
| (2) | 22.6 | 12800 | 566 |
| (3) | 2.1 | 4800 | 2286 |
| (4) | 0.4 | 1600 | 4000 |
| (5) | 2.8 | 12800 | 4571 |
| (6) | 6.8 | 25600 | 3765 |
| (7) | 1.6 | 25600 | 16000 |
| (8) | 0.9 | 204800 | 227556 |

(1): Starting plasma
(2): Heparin elution/treatment with ammonium sulfate
(3): Anion exchange chromatography; non-adsorbed fraction
(4): Anion exchange chromatography; adsorption and elution
(5): Cation exchange chromatography; adsorption and elution
(6): Hydrophobic chromatography; adsorption and elution
(7): HiTrap heparin, adsorption and elution
(8): C4 Reverse phase HPLC For fractionating the obtained active fraction more fully, fractionation was further performed using ion exchange chromatographic carrier Mini Q (manufactured by Pharmacia). A linear gradient elution with sodium chloride was carried out under the condition of 20 mM ethanolamine, pH 9.15. The activity was detected in all the fractions obtained, which also reacted with the antibody prepared in Example 4 as described below. This proved that the active substance was present in various different structures.

Figure 2:
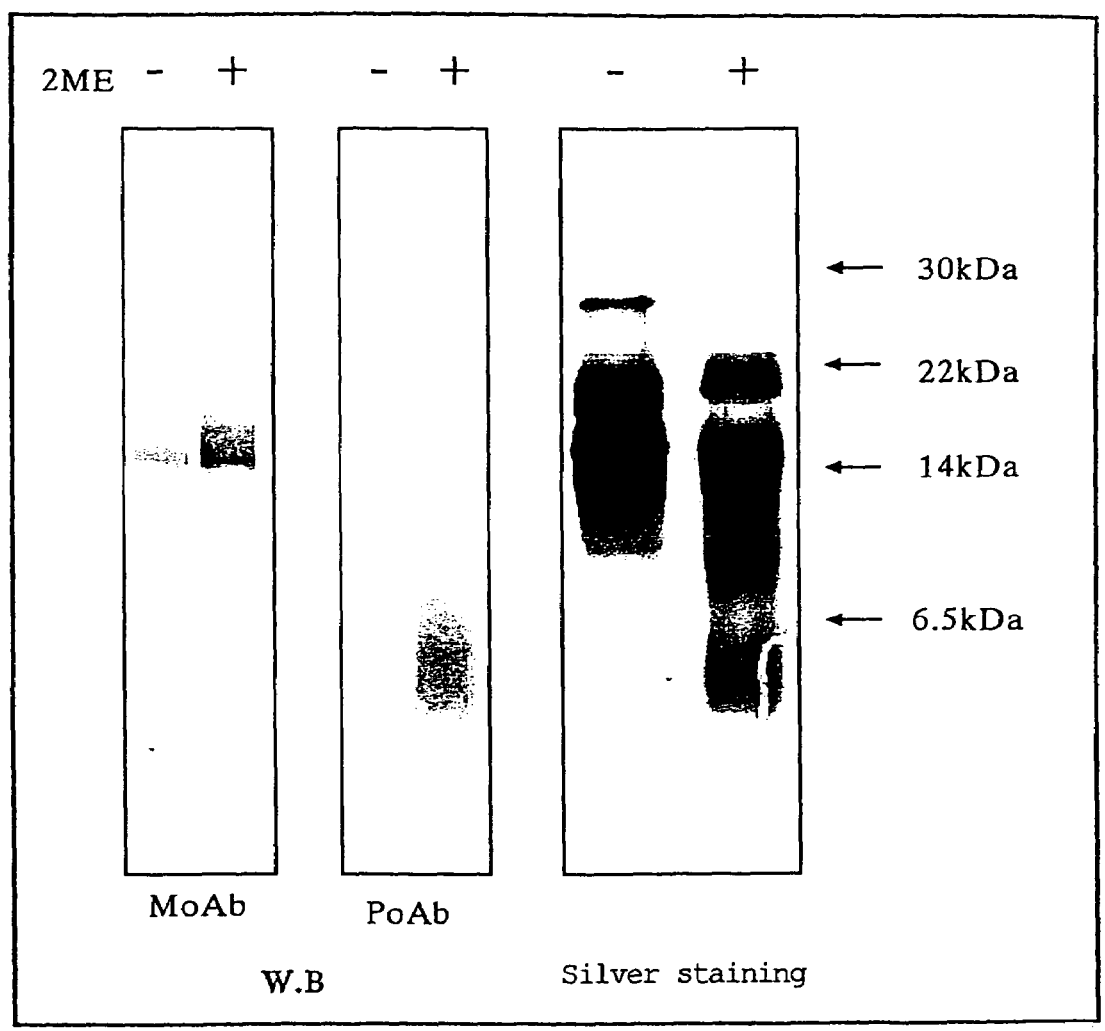
FIG. 2 shows electrophoretograms either with silver staining or Western blotting denoting purity of the purified peptide fragment or a series of purified peptide fragments having a cell death-inhibitory activity of the present invention.

The active substance of interest at this stage, as a result of electrophoretic analysis, had under non-reductive condition several bands at 10 kDa to 30 kDa and under reductive condition at least six bands, i.e. each one band of smear at 3 to 4 kDa and at 7 to 9 kDa, two bands at 13 to 14 kDa, and two bands at 16 to 17 kDa. All these bands could be detected in Western blotting analysis using the antibody described in Example 4. A protein that reacted with the antibody was also detected at the vicinity of 28 to 29 kDa in electrophoresis under non-reductive condition, suggesting that a dimer might possibly be formed. See FIG. 2.

EXAMPLE 3

(Analysis of N-Terminal Sequence of Active Components)

Amino acid sequence analysis with a gas phase sequencer revealed that the active components of the present invention consisted of a peptide comprising the amino acid sequence: Lys Arg Cys Ile Asn Gln Leu Leu Cys Lys Leu Pro Thr Asp Ser Glu Leu Ala Pro Arg Ser Xaa Cys Cys His Cys Arg His Leu (SEQ ID NO: 1) and a peptide comprising the amino acid sequence: Thr Gly Ser Ala Ile Thr Xaa Gln Cys Lys Glu Asn Leu Pro Ser Leu Cys Ser Xaa Gln Gly Leu Arg Ala Glu Glu Asn Ile, wherein Xaa is selenocysteine (SEQ ID NO: 2). A ratio of these peptides was in a range of from 1:1 to 2:1 as estimated from an amount of amino acid residues recovered while sequencing of this fraction. A recovery of amino acid residues from other proteins than these two peptides was 5% or less. These two peptides were separated by gel filtration chromatography and C4 reverse phase HPLC under reduced condition to suggest the presence of molecular species formed by S—S bonding.

Among the peptides separated by C4 HPLC under reduced condition, a peptide having a molecular weight of 3 to 4 kDa, as a result of sequencing analysis, had the amino acid sequence: Lys Arg Cys Ile Asn Gln Leu Leu Cys Lys Leu Pro Thr Asp Ser Glu Leu Ala Pro Arg Ser (SEQ ID NO: 5) and the fraction consisted mainly of 7 to 9 kDa had the amino acid sequence: Thr Gly Ser Ala Ile Thr Xaa Gln Cys Lys Glu Asn Leu Pro Ser Leu Cys Ser Xaa Gln Gly Leu Arg Ala Glu Glu Asn Ile (SEQ ID NO: 2). Both the fractions of 13 to 14 kDa and of 16 to 17 kDa had also the amino acid sequence: Lys Arg Cys Ile Asn Gln Leu Leu Cys Lys Leu Pro Thr Asp Ser Glu Leu Ala Pro Arg Ser (SEQ ID NO: 5). These amino acid sequences corresponded to the fragments starting from the 260th lysine and from the 293rd threonine in the amino acid sequence shown in the following Table 0.2, following the signal sequence, deduced from the cDNA sequence of human selenoprotein P previously published (Hill K. E. et al., Proc. Natl. Acad. Sci. USA, vol. 90, p. 537-541 (1993)).

TABLE 2

Met Trp Arg Ser Leu Gly Leu Ala Leu Ala Leu Cys Leu Leu Pro

Ser Gly Gly Thr (signal sequence)

Glu Ser Gln Asp Gln Ser Ser Leu Cys Lys Gln Pro Pro Ala Trp 15

Ser Ile Arg Asp Gln Asp Pro Met Leu Asn Ser Asn Gly Ser Val 30

Thr Val Val Ala Leu Leu Gln Ala Ser Xaa Tyr Leu Cys Ile Ile 45

Glu Ala Ser Lys Leu Glu Asp Leu Arg Val Lys Leu Lys Lys Glu 60

TABLE 2-continued

```
Gly Tyr Ser Asn Ile Ser Tyr Ile Val VaL Asn His Gln Gly Ile   75

Ser Ser Arg Leu Lys Tyr Thr His Leu Lys Asn Lys Val Ser Glu   90

His Ile Pro Val Tyr Gln Gln Glu Glu Asn Gln Thr Asp Val Trp  105

Thr Leu Leu Asn Gly Ser Lys Asp Asp Phe Leu Ile Tyr Asp Arg  120

Cys Gly Arg Leu Val Tyr His Leu Gly Leu Pro Phe Ser Phe Leu  135

Thr Phe Pro Tyr Val Glu Glu Ala Ile Lys Ile Ala Tyr Cys Glu  150

Lys Lys Cys Gly Asn Cys Ser Leu Thr Thr Leu Lys Asp Glu Asp  165

Phe Cys Lys Arg Val Ser Leu Ala Thr Val Asp Lys Thr Val Glu  180

Thr Pro Ser Pro His Tyr His His Glu His His His Asn His Gly  195

His Gln His Leu Gly Ser Ser Glu Leu Ser Glu Asn Gln Gln Pro  210

Gly Ala Pro Asn Ala Pro Thr His Pro Ala Pro Pro Gly Leu His  225

His His His Lys His Lys Gly Gln His Arg Gln Gly His Pro Glu  240

Asn Arg Asp Met Pro Ala Ser Glu Asp Leu Gln Asp Leu Gln Lys  255

Lys Leu Cys Arg Lys Arg Cys Ile Asn Gln Leu Leu Cys Lys Leu  270

Pro Thr Asp Ser Glu Leu Ala Pro Arg Ser Xaa Cys Cys His Cys  285

Arg His Leu Ile Phe Glu Lys Thr Gly Ser Ala Ile Thr Xaa Gln  300

Cys Lys Glu Asn Leu Pro Ser Leu Cys Ser Xaa Gln Gly Leu Arg  315

Ala Glu Glu Asn Ile Thr Glu Ser Cys Gln Xaa Arg Leu Pro Pro  330

Ala Ala Xaa Gln Ile Ser Gln Gln Leu Ile Pro Thr Glu Ala Ser  345

Ala Ser Xaa Arg Xaa Lys Asn Gln Ala Lys Lys Xaa Glu Xaa Pro  360

Ser Asn
``` wherein Xaa is selenocysteine (SEQ ID NO: 6)

EXAMPLE 4

(Preparation of Antibody to Active Components)

In order to prove that the bands obtained in Example 2 were derived from one and same substance, a polyclonal anti-peptide antibody and a monoclonal antibody were prepared as described below. As a result of Western blotting using these antibodies, all the bands observed in electrophoresis were recognized by the same monoclonal antibody and the anti-peptide antibody to prove that the peptide fragments had the identical, though not uniform, structure.

① Preparation of Anti-Peptide Antibody

For preparing an anti-peptide antibody, the active fraction was subjected to gel filtration and C4 reverse phase HPLC under reduced condition to prepare peptides of 3 to 4 kDa. Then, based on analysis of the amino acid sequence of said peptides, a peptide of 20 amino acid residues was synthesized and used for immunization of rabbit. Specifically, a peptide having the sequence NH₂-Lys Arg Cys Ile Asn Gln Leu Leu Cys Lys Leu Pro Thr Asp Ser Glu Leu Ala Pro Arg-COOH (SEQ ID NO: 4) was synthesized with a peptide synthesizer and purified by C18 reverse phase HPLC. The purified peptide was bound to KLH at a ratio 1:1 using glutaraldehyde and 200 µg of the conjugate was inoculated to two New Zealand white rabbits. Immunization as priming was made once subcutaneously at the back in the presence of Freund's complete adjuvant. Thereafter, three immunizations with subcutaneous inoculation at the back at each two weeks interval followed in the presence of Freund's incomplete adjuvant and the animal were bled. Antiserum was examined for its reactivity with the immunogen by EIA and increase in antibody titer up to as high as 40,000-folds was demonstrated. This antiserum was affinity-purified with a carrier wherein the antigen was bound to agarose to give an anti-peptide antibody that showed the similar reactivity to the antiserum.

② Preparation of Monoclonal Antibody

For immunization as priming, 50 µg of the purified fraction of the active components of the present invention as described in Example 2 was once inoculated intraperitoneally to Balb/c mice in the presence of Freund's complete adjuvant. Thereafter, the mice were twice immunized intraperitoneally in the presence of Freund's incomplete adjuvant at two weeks interval. A week later, the mice were inoculated intravenously with 50 µg of the purified fraction of the active components. Three days after the final immunization, spleen cells were removed from the mice in the conventional manner. Among five mice tested, the spleen cells from two mice showed stronger reactivity with the immunogen in Western blotting using the antiserum but were reduced in number to as low as ⅟₁₀ than normally observed, suggesting that the antibody to immunogen might have affected B cells.

The obtained spleen cells were mixed with myeloma cells P3X63Ag8.U1 (P3U1) (ATCC deposit No. CRL-1597: Curr. Top. Microbiol. Immunol., vol. 81, p. 1 (1978)) at a ratio of 1:1 to 1:2 and centrifuged (1,500 rpm, 5 minutes) Supernatant was discarded and the precipitated cell pellet was sufficiently loosened and thereto was added 1 ml of a polyethylene glycol solution (45% polyethylene glycol 4000, 55% RPMI medium), previously heated to 37° C., while stirring. After incubation at 37° C. for 5 minutes, RPMI medium was slowly added to make a total of 50 ml. After centrifugation (1,300 rpm, 7 minutes), supernatant was discarded and the cell pellet was moderately loosened. Thereto was added 50 ml of Escron CM-B medium (manufactured by Sanko Jun-yaku K.K.) and the cells were moderately suspended with a measuring pipette. Each 100 μl of the cell suspension was distributed to each well of four or five 96-well cell culture plates and incubated in $CO_2$ incubator with 5% carbonic acid gas at 37° C. On the next day, each 100 μl HAT medium (Escron CM-B medium supplemented with $1\times10^4$ M hypoxanthine, $1.5\times 10^{-3}$ M thymidine and $4\times10^{-7}$ M aminopterin) was distributed to each well and incubated in $CO_2$ incubator with 5% carbonic acid gas at 37° C. In a descending order of growth of hybridoma colonies, the culture medium was replaced with HT medium (the HAT medium from which aminopterin was deprived). A portion of the culture supernatant was taken for screening hybridomas of interest by means of the following screening procedures, which consisted of a combination of EIA and Western blotting as described below.

(1) EIA

The synthetic peptidic antigen prepared as described above or purified antigen (2 μg/ml of protein) was added to a 96-well microtiter plate at 50 μl/well and the plate was incubated at 4° C. overnight. The plate was added with 300 μl of 1% BSA (bovine serum albumin) solution and incubated similarly for masking. To the thus prepared antigen-immobilized plate was added culture supernatant of the hybridomas prepared by cell fusion and of the hybridomas after cloning. The plate was incubated at 4° C. for 1.5 hour, washed with PBS three times, and added with a solution of peroxidase-conjugated anti-mouse immunoglobulin (manufactured by Kappel, diluted by 5,000-folds) at 100 μl/well. After incubation at 4° C. for 1 hour, the plate was washed with PBS five times. To the plate was added a TMBZ substrate solution to develop in the conventional manner and absorbance was measured at 450 nm. As such, hybridoma clones that reacted with the purified antigen were screened. Sixteen positive colonies were screened from about 500 hybridomas.

(2) Western blotting

Screening by Western blotting was performed for the positive colonies in EIA. The purified antigen was electrophoresed on 17.5% SDS-polyacrylamide gel and transferred to PVDF membrane. The membrane was excised into 0.4 to 0.5 cm width. Each strip was immersed into the culture supernatant solution of hybridomas and incubated at 37° C. for 1 hour. Strip was then washed with TBST containing 0.05% Tween three times and incubated in a 1:2000 dilution of alkaline phosphatase-conjugated anti-mouse IgG (manufactured by TAGO) at 37° C. for 1 hour. After washing with TBST three times, strip was developed with a color reagent using BCIP/NBT (manufactured by Bio-Rad) and hybridomas showing colored bands of the purified antigen were screened and cloned. The same procedures were employed for the hybridomas after cloning. The above screening provided two hybridoma clones that produced the desired monoclonal antibody.

EXAMPLE 5

(Purification of Selenoprotein P Fragment Using Anti-Selenoprotein P Antibody-Bound Carrier Column)

Figure 3:
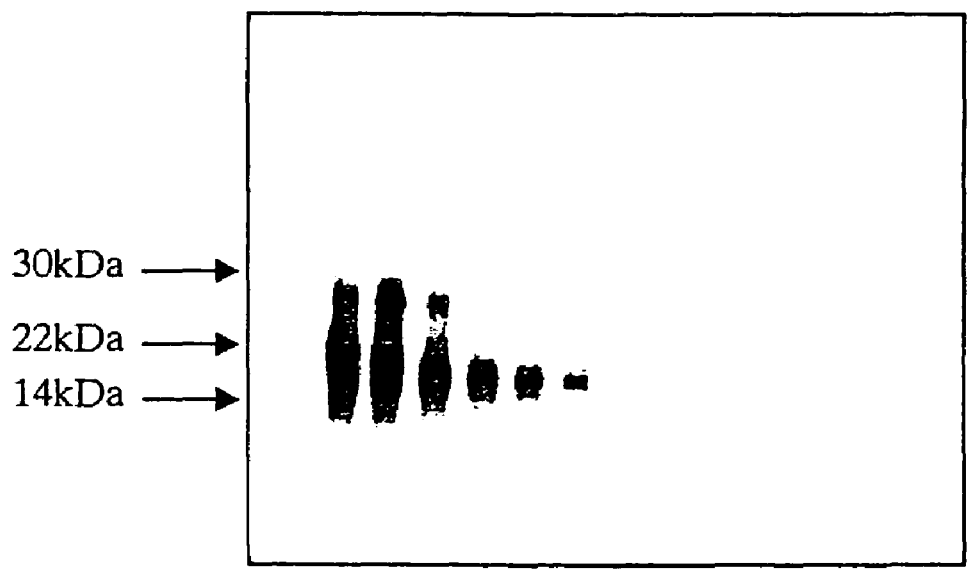
FIG. 3 shows electrophoretogram with silver staining denoting purity of the peptide fragment or a series of peptide fragments having a cell death-inhibitory activity of the present invention, purified with a carrier column to which anti-selenoprotein P antibody is bound.

Heparin Sepharose-binding fraction from plasma was precipitated with 2 M ammonium sulfate. The precipitate was dissolved in more than 5 volumes of 20 mM Tris buffer, pH 8.0. Selenoprotein P present in this solution was adsorbed to an anti-selenoprotein P antibody-bound carrier column in which the anti-selenoprotein P antibody as described in Example 4 was bound to a carrier. The carrier was washed with phosphate buffered saline (PBS) and selenoprotein P was eluted with 20 mM citrate buffer, pH 4.0 containing 4 M urea. The eluate was adsorbed to a cation exchanger (Macro-prep High S, BioRad) equilibrated with 20 mM citrate buffer, pH 4.0. Then, gradient elution was performed with a salt concentration of sodium chloride and a fraction of selenoprotein P fragment having the cell death-inhibitory activity was recovered. At this stage, a full-length selenoprotein P could also be obtained but showed the cell death-inhibitory activity per proteins that was much lower than that of the fragment thereof. According to the procedures as described herein, purification may be carried in a short time and hence selenoprotein P fragments could be obtained with higher cell death-inhibitory activity per proteins. The fragments obtained at this stage were also a fraction of a mixture containing various molecular species with varied sizes depending on the presence or absence of glycosylation, intermolecular bonding, or inner cleavage, etc. They were a group of selenoprotein P fragments that showed a size ranging from 10 to 30 kDa in electrophoresis under non-reductive condition. See FIG. 3.

EXAMPLE 6

(Treatment of Mini Q Active Fraction with N-Glycosidase)

Figure 4:
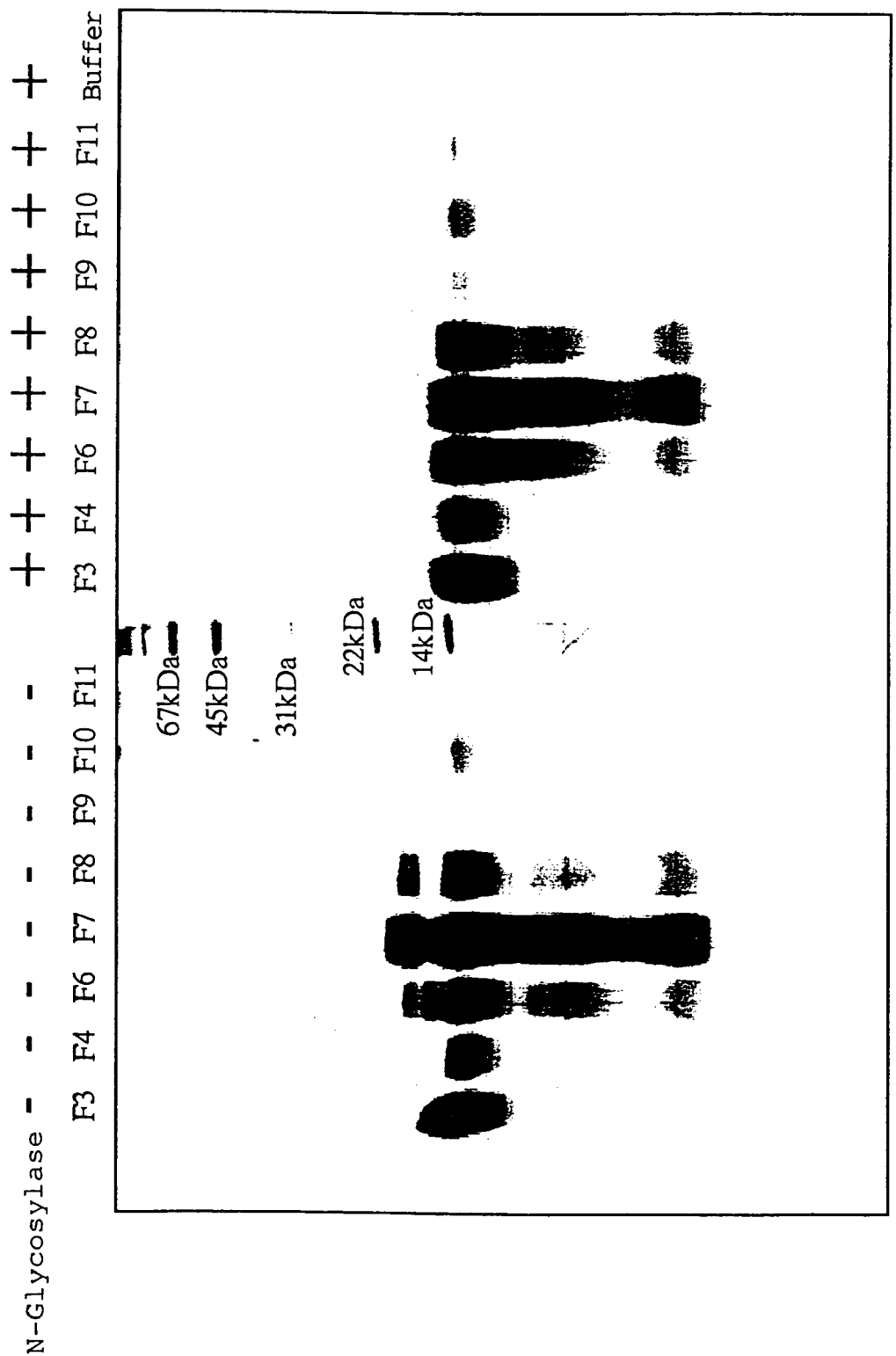
FIG. 4 shows electrophoretogram denoting behavior of the purified peptide fragment or a series of purified peptide fragments having a cell death-inhibitory activity of the present invention after treatment with N-glycosidase.

In order to investigate the presence of glycosylation in the active fraction, the active fraction obtained by mini Q fractionation was treated with N-glycosidase F to cleave N-type glycosylation, if any. The treatment was done in 150 mM Tris, pH 7.4. As a result, it was proved that the two peptides at 16 to 17 kDa shifted to the size of 13 to 14 kDa. No significant change was observed for the other peptides. See FIG. 4.

EXAMPLE 7

(Reductive Carboxymethylation)

For obtaining more detailed information, the peptide fragment or a series of peptide fragments of the present invention were subjected to reductive carboxymethylation followed by separation with reverse phase C4 HPLC. The obtained peptide fragments were electrophoresed and analyzed for their amino acid sequences. Electrophoresis revealed that two peptides, a size of which was expected to be 7 to 9 kDa prior to treatment, shifted to a distance corresponding to 10 to 12 kDa due to reductive carboxymethylation. It was proved by the reactivity with the anti-peptide antibody that only two peptide fragments, i.e. the peptide fragment of F3 and the fragment of F2 of 16 to 18 kDa, which was expected to show a molecular weight of 10 to 12 kDa prior to treatment, did not comprise the peptide fragment having the amino acid sequence: Lys Arg Cys Ile Asn Gln Leu Leu Cys Lys Leu Pro Thr Asp Ser Glu Leu Ala Pro Arg (SEQ ID NO: 4).

As a result of amino acid sequence analysis, the peptide fragments contained in the above F2 and F3 fractions had the amino acid sequence: Thr Gly Ser Ala Ile Thr Xaa Gln Cys Lys Glu Asn Leu Pro Ser Leu Cys Ser Xaa Gln (SEQ ID NO: 7) wherein Xaa was selenocysteine. The F2 band at 16 to 18 kDa shifted to the F3 band upon treatment with N-glycanase to thereby prove that the F2 band was a glycosylated form of the F3 band. All the fractions that were reacted with the anti-peptide antibody, including the fragments with peptides, a molecular weight of which shifted upon N-glycanase treatment, had the amino acid sequence: Lys Arg Cys Ile Asn Gln Leu Leu Cys Lys Leu Pro Thr Asp Ser Glu Leu Ala Pro Arg Ser (SEQ ID NO: 5).

Figure 5:
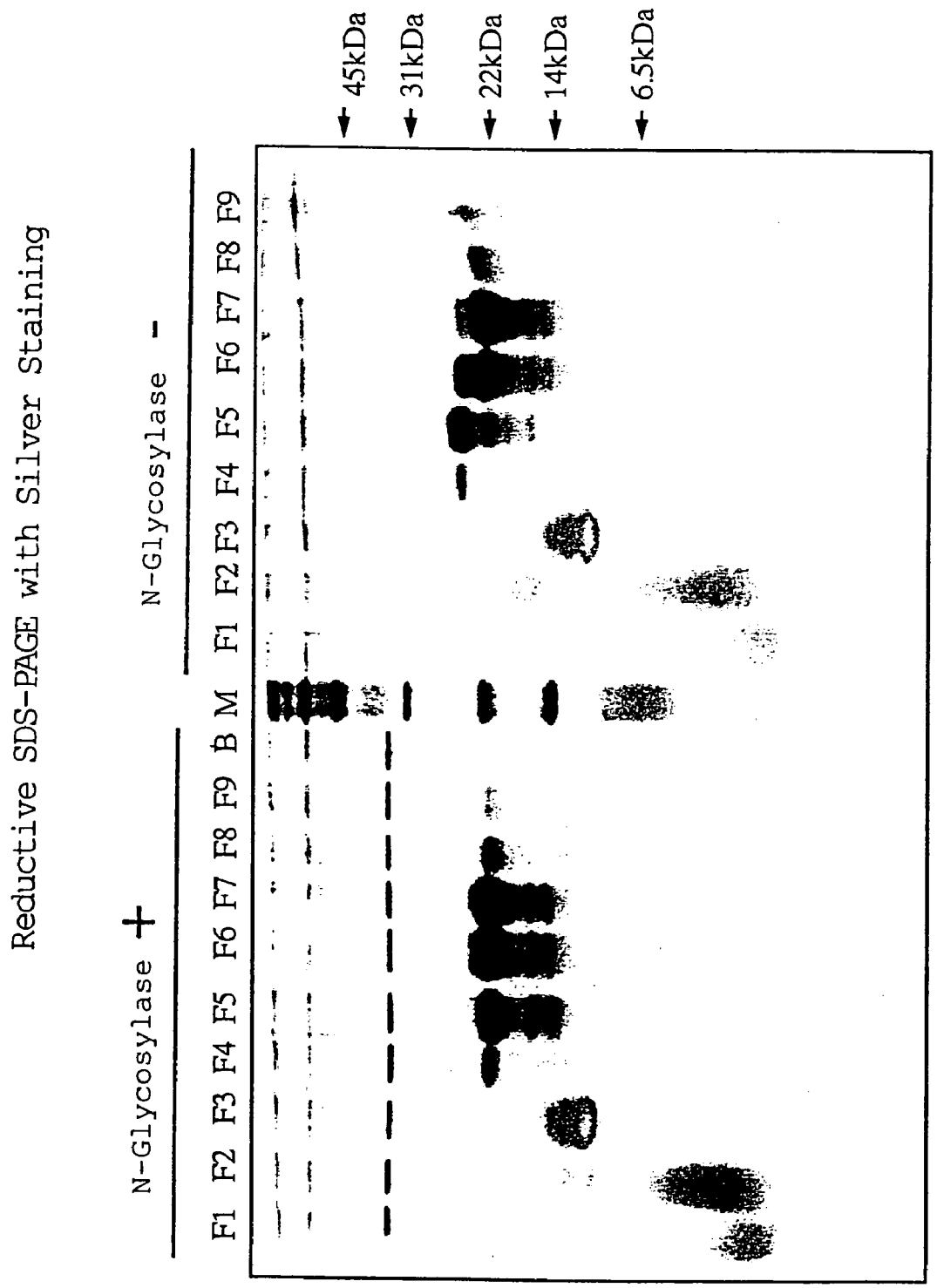
FIG. 5 shows electrophoretogram with silver staining denoting behavior of the purified peptide fragment or a series of purified peptide fragments having a cell death-inhibitory activity of the present invention after reductive carboxymethylation.
Figure 6:
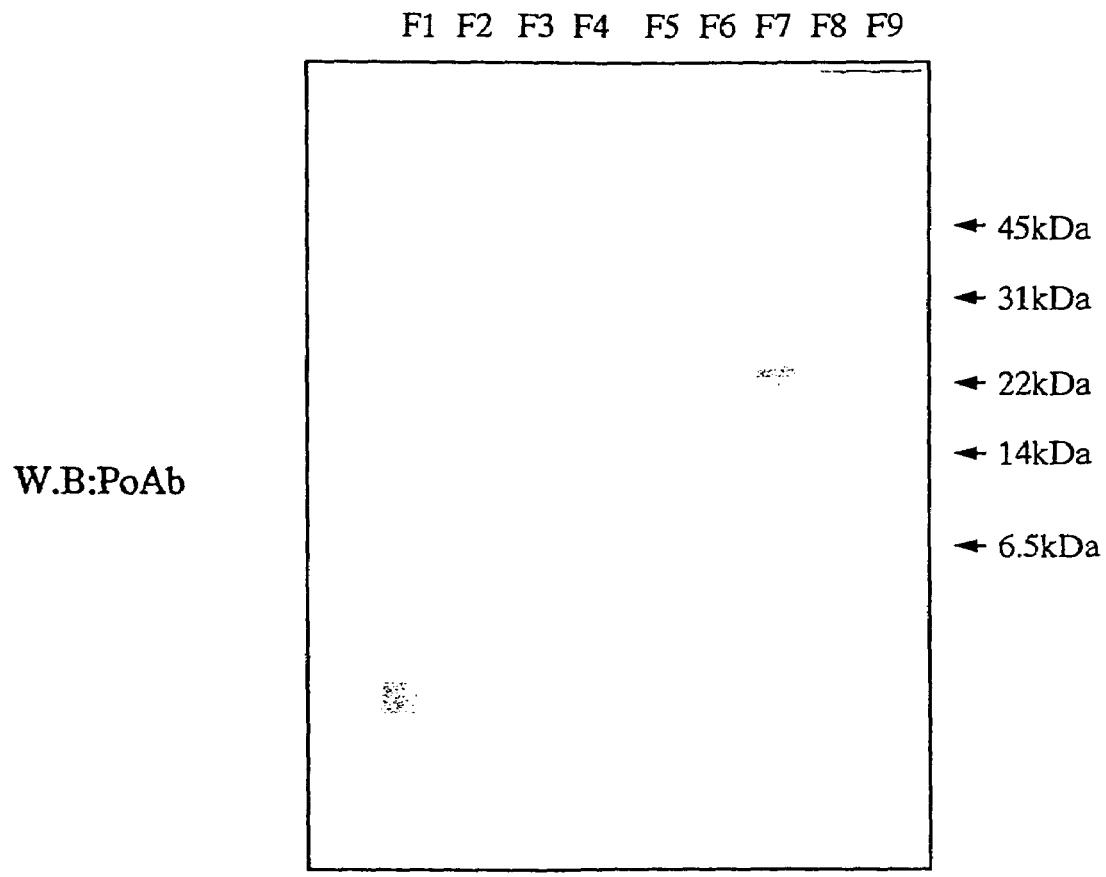
FIG. 6 shows electrophoretogram with Western blotting denoting behavior of the purified peptide fragment or a series of purified peptide fragments having a cell death-inhibitory activity of the present invention after reductive carboxymethylation.

Taken the results obtained above and in Example 3 together, among the peptide fragments corresponding to each of (1) 3 to 4 kDa, (2) 7 to 9 kDa, (3) 10 to 12 kDa, (4) 13 to 14 kDa and (5) 16 to 17 kDa, of the active substance, it is recognized that the bands (1), (4) and (5) are fragments starting from the 260th lysine whereas the bands (2) and (3) are fragments starting from the 293rd threonine. From the fact that the peptide fragments (1), (2) and (3) were not obtained under non-reductive condition, it was proved that these peptide fragments were formed after inner cleavage of the peptide fragments (4) and (5) having unit structures bound through S—S bonding. It was also proved that the peptide fragment (5) was a glycosylated form of (4) viewing that the band (5) shifted to the band (4) upon N-glycanase treatment and that the band (5) was recognized by the antibody to the band (1). Moreover, bands of different sizes, not derived from glycosylation, were detected at the vicinity of each band, and hence, it was estimated that several other peptide fragments with different size derived from the C-terminal existed. See FIGS. 5 and 6.

EXAMPLE 8

(Comparison of Activity with Other Proteins)

Figure 7:
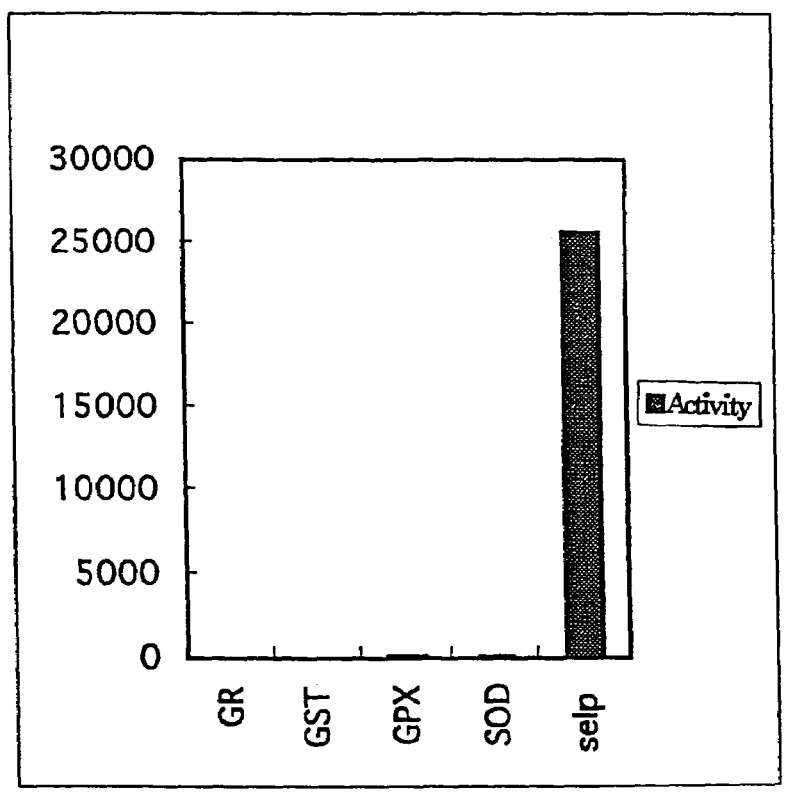
FIG. 7 shows results of comparative experiment on the cell death-inhibitory activity of the peptide fragment or a series of peptide fragments of the present invention with other proteins.

Selenoproteins and related antioxidant proteins, not belonging to the active components of the present invention, were examined for their cell death-inhibitory activity. Glutathione peroxidase (manufactured by SIGMA) as antioxidant selenoprotein, glutathione reductase (manufactured by Oriental Yeast K.K.), glutathione S transferase (manufactured by SIGMA), and superoxide dismutase (manufactured by Seikagaku Kogyo K.K.) as other related antioxidant proteins were used to test their cell death-inhibitory activity in Dami cells for comparison. Each 70 μM of the samples was employed for measurement. Assay revealed some activity observed for glutathione peroxidase and superoxide dismutase. However, in comparison with the peptide fragment and a series of peptide fragments having the cell death-inhibitory activity of the present invention as characterized herein, they showed the activity as low as about 1/100 of the present invention. This obviously demonstrated the superiority of the peptide fragment and a series of peptide fragments having the cell death-inhibitory activity of the present invention in their activity. See FIG. 7.

In addition, the full-length selenoprotein P prepared with the antibody affinity column as described above was estimated for its cell death-inhibitory activity in the same assay system for comparison. It was demonstrated that the peptide fragment and a series of peptide fragments of the present invention, a fragmented form of selenoprotein P, had the specific activity superior to that of the full-length selenoprotein P by more than 80-times, proving significance of "fragmentation". See Table 3 below.

TABLE 3

| Sample | Protein conc. (μg/ml) | Activity | Specific activity |
| --- | --- | --- | --- |
| Full-length selenoprotein P | 40 | <100 | <2500 |
| Peptide fragment of the invention | 10 | 2000 | 200000 |

EXAMPLE 9

(Comparison of Activity with Other Antioxidants)

It was estimated to what extent vitamin E, known as being useful as an antioxidant to lipid oxidation, and catalase, acting for removal of hydrogen peroxide, could inhibit cell death induced in the assay system of the present invention while serum free culture in the presence of HSA.

To 1 ml Dami cells (1×10⁶ cells/dish/3 ml), which can be subcultured in serum free medium SFO3 (manufactured by Sanko Jun-yaku K.K.) containing 0.05 μM 2ME and 0.1% BSA, was added 2 ml 1:2:2 mixed medium (SA medium) of RPMI 1640/D-MEM/F-12. The cells were cultured for three days and recovered for assay. The cells were washed twice with 50% PBS/SA/0.03% HSA (manufactured by SIGMA) and suspended in the same medium at 3×10⁴ cells/ml. The cell suspension was added to a 96-well plate in each 190 μl for wells for sample addition or in each 100 μl for wells for serial dilution.

Figure 8:
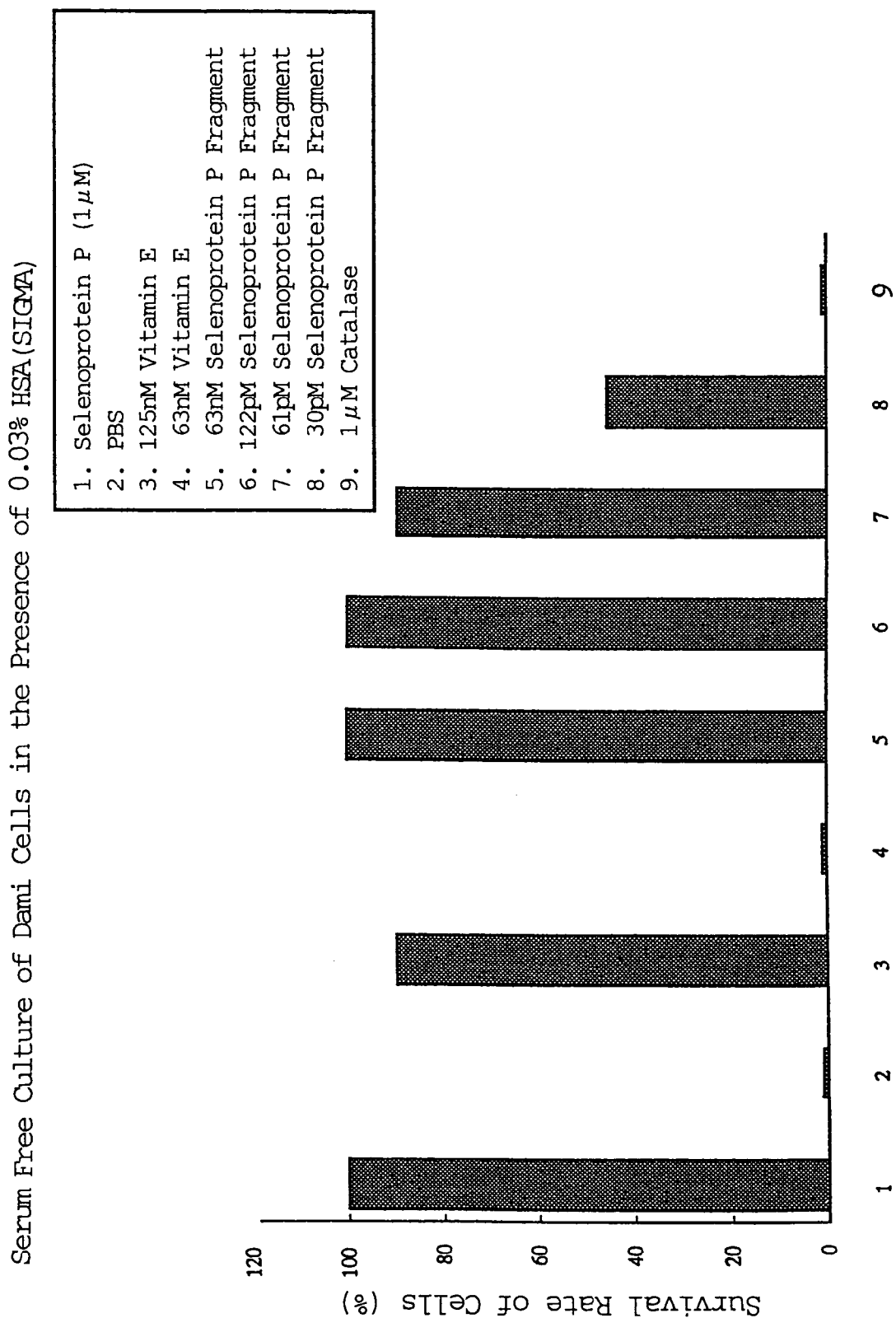
FIG. 8 shows results of comparative experiment on the cell death-inhibitory activity of the peptide fragment or a series of peptide fragments of the present invention with other antioxidants.

To the wells for sample addition was added each 10 μl of assay sample, i.e. 20 μM vitamin E, catalase or the selenoprotein P fragment and, after stirring, a serial dilution was made with the wells containing 100 μl cell suspension. The plate was incubated at 37° C. in CO₂ incubator for 4 to 5 days followed by estimation. For estimation, a sample concentration necessary for cell death inhibition was compared to each other on Day 4 and thereafter. It was demonstrated that catalase showed no cell death-inhibitory activity whereas vitamin E inhibited cell death up to 125 nM but could not at 60 nM. The selenoprotein P fragment could inhibit cell death up to 60 μM. From the fact that vitamin E did inhibit cell death in the assay system of the present invention, it was estimated that peroxidization of fatty acids bound to HSA (SIGMA) might be responsible for cell death induction. Moreover, it was expected that the selenoprotein P fragment, which inhibited cell death more effectively than vitamin E, would also act much more efficiently to events to which vitamin E was know to be effective. See FIG. 8.

EXAMPLE 10

(Inhibitory Activity to Cell Death Induced by Fatty Acid)

Any long-chain fatty acid with at least two double bonds including, for example, eicosadienoic acid, dihomo-γ-linolenic acid, docosadienoic acid, docosatrienoic acid, adrenic acid, eicosapentaenoic acid, docosahexaenoic acid, linoleic acid, linolenic acid and arachidonic acid induced cell death at 10 μM in serum free culture in the absence of selenoprotein P. Among these, the most potent cell death inducer, arachidonic acid, linoleic acid and linolenic acid were thoroughly investigated for their concentration that induced cell death as well as a concentration of selenoprotein P necessary for inhibiting the cell death.

To 1 ml Dami cells (1×10⁶ cells/dish/3 ml) which can be subcultured in serum free medium SFO3 (manufactured by Sanko Jun-yaku K.K.) containing 0.05 µM 2ME and 0.1% BSA, was added 2 ml 1:2:2 mixed medium (SA medium) of RPMI 1640/D-MEM/F-12. The cells were cultured for three days and recovered for assay. The cells were washed twice with SA/0.05% fatty acid free BSA (manufactured by Wako Jun-yaku K.K.) and suspended at $3 \times 10^4$ cells/ml in the same medium containing 2 to 16 µM arachidonic acid, linoleic acid or linolenic acid. The cell suspension was added to a 96-well plate in each 198 µl for wells for sample addition or in each 100 µl for wells for serial dilution.

To the wells for sample addition was added each 2 µl of 100 µM assay sample and, after stirring, a serial dilution was made with the wells containing 100 µl cell suspension. The plate was incubated at 37° C. in $CO_2$ incubator for 4 to 5 days. Cell death induction and inhibition of cell death by selenoprotein P fragment were estimated with 1 µM selenoprotein P and effective concentration thereof by serial dilution.

Figure 9:
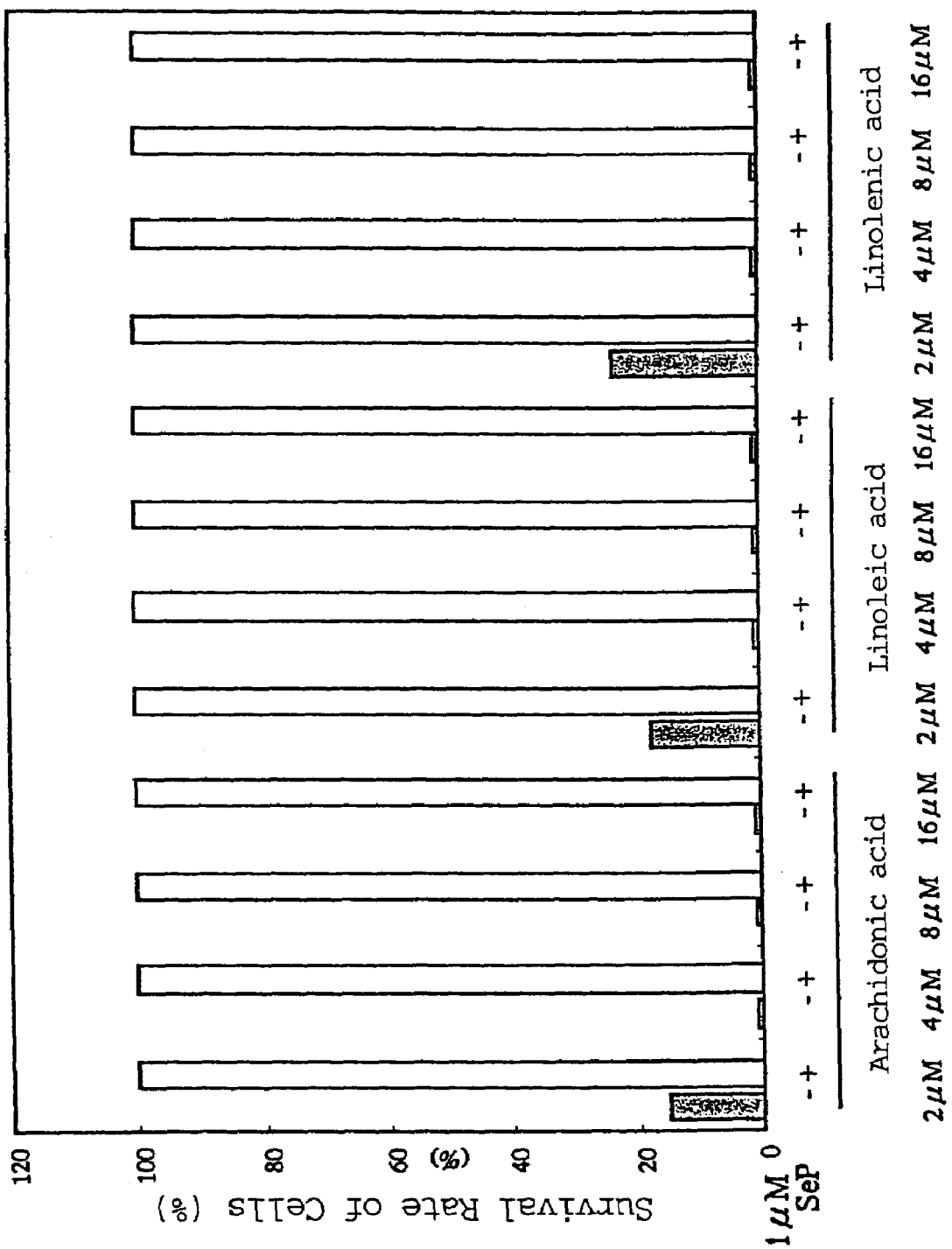
FIG. 9 shows the cell death-inhibitory activity of the peptide fragment or a series of peptide fragments of the present invention against cell death induced by fatty acids.
Figure 10:
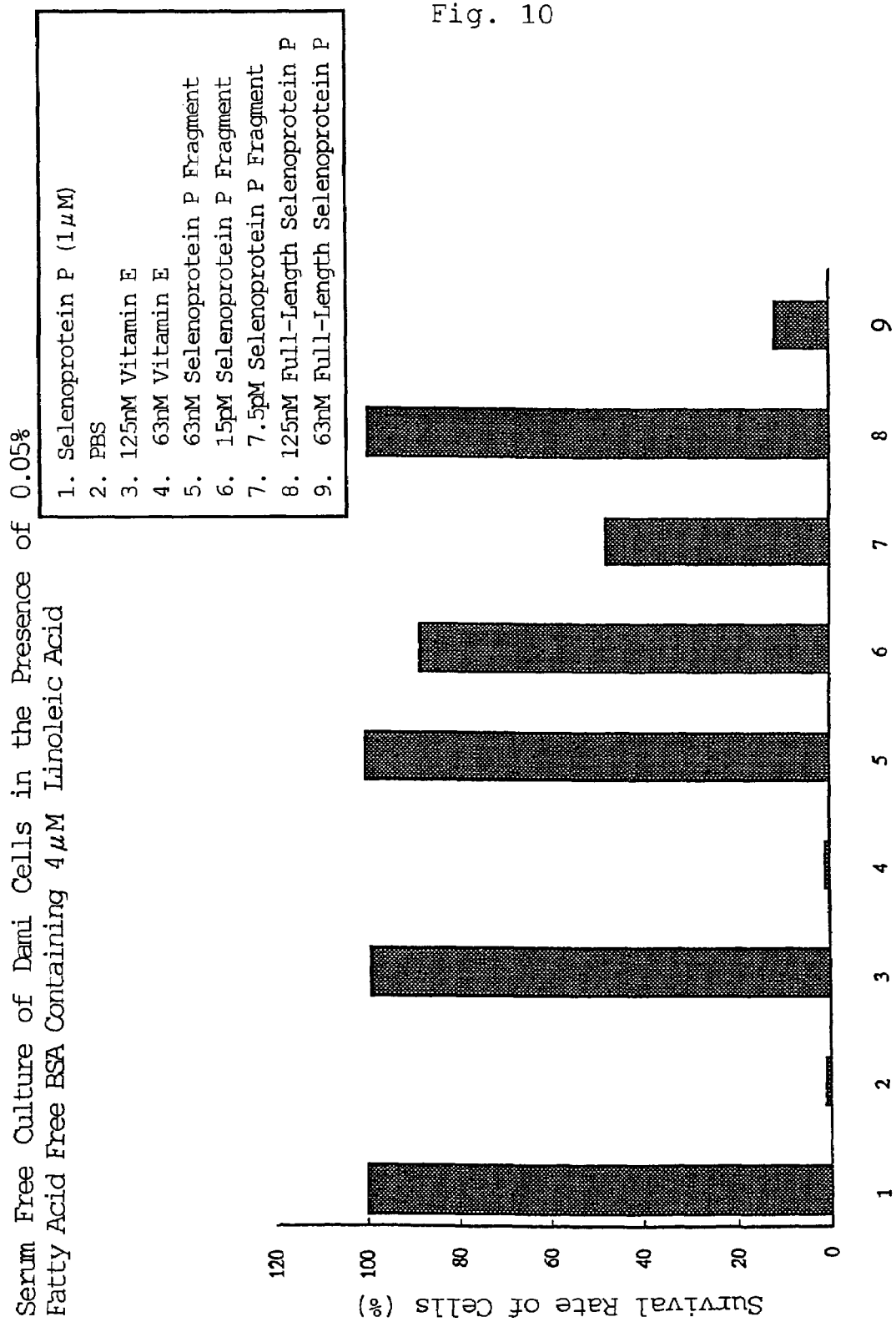
FIG. 10 shows results of comparative experiment on the cell death-inhibitory activity of the peptide fragment or a series of peptide fragments of the present invention with other antioxidants, typically vitamin E, against cell death induced by fatty acids.

It was demonstrated that cell death was induced in serum free culture of the cells in the presence of 4 µM or more multivalent unsaturated fatty acids such as arachidonic acid or linoleic acid and was completely inhibited by 1 µM selenoprotein P fragment. See FIG. 9. As compared to vitamin E which inhibited cell death in the presence of 4 µM linoleic acid at an effective concentration of about 100 nM, a full-length selenoprotein P and selenoprotein P fragment inhibited at an effective concentration of about 100 nM and 10 pM, respectively. Thus, the selenoprotein P fragment could inhibit cell death at much lower effective concentration. See FIG. 10. From the fact that vitamin E, an antioxidant, did inhibit cell death, it was estimated that fatty acids, upon being peroxidized either intracellularly or extracellularly, damaged cells leading to cell death whereas the selenoprotein P fragment efficiently prevented these events from occurring.

Then, various enzymes related to oxidation/reduction were investigated for their activity to inhibit cell death induced in Dami cells in the presence of 4 µM linoleic acid or linolenic acid. The enzymes tested include glutathione peroxidase, superoxide dismutase, glutathione reductase, glutathione-S-transferase, and catalase. Only glutathione peroxidase could inhibit cell death at 250 nM or more in the presence of linoleic acid and at 500 nM or more in the presence of linolenic acid. The other enzymes, however, could not inhibit cell death even at 1 µM or more. The fact that the selenoprotein P fragment could inhibit cell death at as low as 10 pM in the same assay condition proved prominent efficacy of the selenoprotein P fragment. By varying a concentration of fatty acids in induction of cell death, influence of fatty acids to various types of cells with different sensitivity or influence of selenoprotein P thereto could be observed. Usually, cell death is induced by the addition of 20 µM linoleic acid and, if cell death is not induced by this condition, selenoprotein P is likely to be expressed. Using this system, the inhibitory activity to cell death induced by fatty acids can be estimated in various types of cells. This system was considered to reflect the similar events to cell death induced by adding HSA (SIGMA).

Hitherto, the selenoprotein P fragment of the present invention was proved to be effective in megakaryoblasts cell lines (Dami), T cell-derived cell lines (Molt4, CEM, Jurkat), B cell-derived cell lines (P3X63AG8.653, P3X63AG8.U1), liver-derived cell lines (HepG2), nervous system-derived cell lines (IMR 32), kidney-derived cell lines (CRL 1932), etc. Thus, it was highly expected that the selenoprotein P fragment could also exert cell death-inhibitory activity to the cells from the immune system, the nervous system or the hemopoietic system, or from the organs.

EXAMPLE 11

(Effect of Cell Death-Inhibitory Substance as Additive to Cell Culture)

Various cell lines including megakaryoblasts strains: Dami, hepatocyte cell strains: HepG2, uterus-derived cell strains: Hela, kidney-derived cell strains: CRL 1932, histic lymphocyte-derived cell lines: U937, T cell-derived cell lines: Jurkat, Molt4 and CEM, fibroblast-derived cell lines: L929, monocyte-derived cell lines: THP-1, B cell-derived cell lines: P3X63AG8.653 and P3X63AG8.U1, and nervous system-derived cell lines: IMR32 were cultured in RPMI 1640/D-MEM/F-12 (1:2:2) free from transferrin, insulin and sodium selenite in the presence or absence of the selenoprotein P fragment. It was demonstrated that exacerbation of cellular conditions was not observed or at least inhibited in the presence of the selenoprotein P fragment in all the types of cells tested. See Table 4. Moreover, in the presence of transferrin and insulin, the cellular conditions could be maintained in all the types of cells tested. Additional presence of 0.05% BSA was found to be more efficacious.

When Jurkat cells were cultured in the presence of 5% human serum wherein selenoprotein P had perfectly been removed with a carrier to which anti-selenoprotein P antibody was immobilized, growth of said cells was exacerbated and decrease in intracellular glutathione peroxidase activity, a kind of intracellular antioxidant enzyme, was observed. However, addition of the selenoprotein P fragment to this culture system could restore the cellular growth and the glutathione peroxidase activity to normal level. A similar effect could also be observed for sodium selenite but the effect of the selenoprotein P fragment was much excellent. Ebselen, a kind of selenium compounds, had no equivalent effect. Thus, it was demonstrated that the selenoprotein P fragment could replace sodium selenite and be used as additives to cell culture.

TABLE 4

Effect of selenoprotein P fragment in serum free culture

|  | Dami | HepG2 | HeLa | CRL1932 | U937 | Jurkat | Molt4 |
|---|---|---|---|---|---|---|---|
| SeP (+) | ◎ | ○ | ○ | ◎ | ◎ | ○ | ○ |
| SeP (−) | ○ | X | Δ | Δ | ○ | X | X |

|  | CEM | L929 | THP-1 | P3X63AG8.653 | P3X63AG8.U1 | IMR32 |
|---|---|---|---|---|---|---|
| SeP (+) | ○ | ◎ | ◎ | Δ | Δ | ○ |
| SeP (−) | X | ○ | ○ | X | X | Δ |

◎: Best in cellular conditions
○: Good in cellular conditions
Δ: Cells with damage
X: Cell death
Sep: Selenoprotein P fragment

The invention claimed is:

1. An isolated or purified monoclonal antibody to a peptide fragment of selenoprotein P having cell death-inhibitory activity, said peptide fragment consisting of SEQ ID NO: 3.

2. The isolated or purified monoclonal antibody of claim 1, wherein said peptide fragment: consists of the amino acid sequence of the formula (I):

Lys Arg Cys Ile Asn Gln Leu Leu Cys Lys Leu Pro Thr Asp Ser Glu Leu Ala Pro Arg Ser Xaa Cys Cys His Cys Arg His Leu (SEQ ID NO: 1), or the amino acid sequence of the formula (II):

Thr Gly Ser Ala Ile Thr Xaa Gin Cys Lys Glu Asn Leu Pro Ser Lou Cys Ser Xaa Gln Gly Leu Arg Ala Glu Glu Asn Ile (SEQ ID NO: 2)

wherein Xaa is selenocysteine.

3. The isolated or purified monoclonal antibody of claim 1, wherein said peptide fragment derived from plasma proteins.

4. The isolated or purified monoclonal antibody of claim 1, wherein said peptide fragment (a) is recovered in fractions of molecular weight 10 kDa to 30 kDa by molecular size fractionation with membrane; (b) has structures showing isoelectnc points at between pH 7 and pH 8 and at pH 8 or more in blood as a result of testing of binding to ion exchange resin; (c) shows two bands at molecular weight 13 to 14 kDa and two bands at 16 to 17 kDa, the latter being a glycosylated form of the former, in non-reductive SDS-PAGE; and (d) has a band pattern of 3 to 4 kDa, 7 to 9 kDa and 10 to 12 kDa in SDS-PAGE under reductive condition in addition to the bands in (c).

* * * * *

UNITED STATES PATENT AND TRADEMARK OFFICE
CERTIFICATE OF CORRECTION

PATENT NO. : 7,598,349 B2 Page 1 of 1
APPLICATION NO. : 11/185859
DATED : October 6, 2009
INVENTOR(S) : Hirashima et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 602 days.

Signed and Sealed this

Twenty-eighth Day of September, 2010

David J. Kappos
*Director of the United States Patent and Trademark Office*